US011082807B2

United States Patent
Theurer et al.

(10) Patent No.: US 11,082,807 B2
(45) Date of Patent: *Aug. 3, 2021

(54) HARDWARE SYSTEM FOR ACTIVE RFID IDENTIFICATION AND LOCATION TRACKING

(71) Applicant: General Electric Company, Schenectady, NY (US)

(72) Inventors: Charles Theurer, Niskayuna, NY (US); Brandon Good, Niskayuna, NY (US); Shaopeng Liu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,318

(22) Filed: Apr. 6, 2020

(65) Prior Publication Data

US 2020/0236509 A1     Jul. 23, 2020

Related U.S. Application Data

(63) Continuation of application No. 16/165,686, filed on Oct. 19, 2018, now Pat. No. 10,616,721, which is a
(Continued)

(51) Int. Cl.
*H04W 24/00*     (2009.01)
*H04W 4/029*     (2018.01)
(Continued)

(52) U.S. Cl.
CPC .......... *H04W 4/029* (2018.02); *G01S 5/0284* (2013.01); *G01S 5/0289* (2013.01); *G06K 7/10425* (2013.01); *G06Q 10/087* (2013.01); *G16H 40/20* (2018.01); *G16H 40/63*
(2018.01); *G16Z 99/00* (2019.02); *H04L 43/106* (2013.01); *H04L 67/18* (2013.01); *H04W 4/025* (2013.01);
(Continued)

(58) Field of Classification Search
CPC ......... H04W 4/02; H04W 4/04; H04W 48/04; H04W 64/00; H04W 84/18
USPC .................................. 455/456.1, 41.1, 41.2
See application file for complete search history.

(56) References Cited

U.S. PATENT DOCUMENTS 7,030,731 B2    4/2006   Lastinger et al.
7,312,752 B2   12/2007   Smith
(Continued)

FOREIGN PATENT DOCUMENTS

WO        0060374      10/2000
WO     2015097314      7/2015

OTHER PUBLICATIONS

United States Patent and Trademark Office, "Non-Final office action", issued in connection with U.S. Appl. No. 14/808,624, dated Jun. 30, 2016, 17 pages.
(Continued)

*Primary Examiner* — Temica M Beamer

(57) ABSTRACT

Systems and methods for facilitating proximity detection and location tracking using a hub or bridge are disclosed. An example apparatus is to receive a message from a beacon at a second location within a proximity area of the apparatus, the message indicative of the second location and identifying the beacon; and relay the message to a location server to determine asset location.

22 Claims, 15 Drawing Sheets

Related U.S. Application Data continuation of application No. 15/464,742, filed on Mar. 21, 2017, now Pat. No. 10,117,059, which is a continuation of application No. 14/808,624, filed on Jul. 24, 2015, now Pat. No. 9,641,969.

(60) Provisional application No. 62/029,252, filed on Jul. 25, 2014.

(51) Int. Cl.

| | | |
|---|---|---|
| *G01S 5/02* | (2010.01) | |
| *G06Q 10/08* | (2012.01) | |
| *G16H 40/63* | (2018.01) | |
| *G16H 40/20* | (2018.01) | |
| *G16Z 99/00* | (2019.01) | |
| *G06K 7/10* | (2006.01) | |
| *H04L 29/08* | (2006.01) | |
| *H04W 4/80* | (2018.01) | |
| *H04L 12/26* | (2006.01) | |
| *H04W 4/02* | (2018.01) | |
| *G16H 40/40* | (2018.01) | |
| *H04W 84/12* | (2009.01) | |

(52) U.S. Cl.
CPC .............. *H04W 4/80* (2018.02); *G16H 40/40* (2018.01); *H04W 84/12* (2013.01)

(56) References Cited

U.S. PATENT DOCUMENTS

| | | | |
|---|---|---|---|
| 7,586,413 | B2 | 9/2009 | Davis |
| 8,319,635 | B2 | 11/2012 | Perkins et al. |
| 8,457,656 | B2 | 6/2013 | Perkins et al. |
| 8,712,330 | B2 | 4/2014 | Desai et al. |
| 8,762,519 | B2 | 6/2014 | Thomson et al. |
| 8,847,754 | B2 | 9/2014 | Buchheim et al. |
| 8,948,782 | B2 | 2/2015 | Shang et al. |
| 9,031,577 | B2 | 5/2015 | Mirzaei et al. |
| 9,277,018 | B2 | 3/2016 | Kotecha et al. |
| 9,374,667 | B1 | 6/2016 | Jorgensen et al. |
| 2006/0261951 | A1 | 11/2006 | Koemer et al. |
| 2010/0090901 | A1 | 4/2010 | Smith et al. |
| 2010/0188211 | A1 | 7/2010 | Brommer et al. |
| 2011/0080264 | A1 | 4/2011 | Clare et al. |
| 2012/0171960 | A1 | 7/2012 | Dshinsky et al. |
| 2013/0127615 | A1 | 5/2013 | Snodgrass |
| 2013/0229263 | A1 | 9/2013 | Graczyk et al. |
| 2014/0192724 | A1* | 7/2014 | Turunen ............ H04W 74/0808 370/329 |
| 2014/0327521 | A1 | 11/2014 | Chen |
| 2015/0105099 | A1 | 4/2015 | Luo et al. |
| 2015/0235550 | A1 | 8/2015 | Pelland et al. |
| 2015/0382153 | A1 | 12/2015 | Otis et al. |
| 2016/0029160 | A1 | 1/2016 | Theurer et al. |
| 2017/0025615 | A1 | 1/2017 | Seo et al. |
| 2017/0195852 | A1 | 7/2017 | Theurer et al. |
| 2017/0229003 | A1* | 8/2017 | Borke .................... G16H 40/20 |
| 2018/0296899 | A1 | 10/2018 | Hansen |
| 2019/0053007 | A1 | 2/2019 | Theurer et al. |

OTHER PUBLICATIONS

United States Patent and Trademark Office, "Notice of Allowance", issued in connection with U.S. Appl. No. 14/808,624, dated Dec. 21, 2016, 25 pages.

Internationa Bureau, "International Search Report and Written Opinion" issued in connection with International Patent Application No. PCT/US2016/042946, dated Nov. 1, 2016. 11 pages.

United States Patent and Trademark Office, "Notice of Allowance", issued in connection with U.S. Appl. No. 14/808,801, dated Oct. 17, 2016, 25 pages.

United States Patent and Trademark Office, "Notice of Allowance", issued in connection with U.S. Appl. No. 15/464,742, dated Jun. 29, 2018, 14 pages.

United States Patent and Trademark Office, "Non-Final Office action", issued in connection with U.S. Appl. No. 15/464,742, dated Jan. 12, 2018, 20 pages.

United States Patent and Trademark Office, "Non-Final Office action", issued in connection with U.S. Appl. No. 16/165,686, dated Jun. 26, 2019, 24 pages.

United States Patent and Trademark Office, "Notice of Allowance", issued in connection with U.S. Appl. No. 16/165,686, dated Oct. 22, 2019, 17 pages.

European Patent Office, "Extended European Search Report," issued in connection with EP Patent application No. 16831062.1, dated Apr. 18, 2019, 10 pages.

\* cited by examiner

HARDWARE SYSTEM FOR ACTIVE RFID IDENTIFICATION AND LOCATION TRACKING

RELATED APPLICATIONS

This patent arises from a continuation of U.S. patent application Ser. No. 16/165,686, filed on Oct. 19, 2018, entitled "Wireless Bridge Hardware System For Active RFID Identification and Location Tracking", which claims the benefit of priority to U.S. patent application Ser. No. 15/464,742, filed on Mar. 21, 2017, entitled "Wireless Bridge Hardware System For Active RFID Identification and Location Tracking", which claims the priority to U.S. patent application Ser. No. 14/808,624, filed on Jul. 24, 2015, entitled "Wireless Bridge Hardware System For Active RFID Identification and Location Tracking", which claims priority to U.S. Provisional Patent Application No. 62/029,252, filed on Jul. 25, 2014, entitled "Hospital Tracking Network" each of which are hereby incorporated herein by reference in their entireties.

TECHNICAL FIELD

Embodiments of the present disclosure relate generally to radio frequency identification and, more particularly, but not by way of limitation, to integrating radio frequency identification with a wireless network.

BACKGROUND

Radio-frequency identification (RFID) is the wireless use of electromagnetic fields to transfer data, for the purposes of automatically identifying and tracking tags attached to objects. The tags contain electronically stored information. An RFID reader includes a receiver that can decode the electronically stored information. Some tags are powered by electromagnetic induction from magnetic fields produced near the reader. Some types collect energy from the interrogating radio waves and act as a passive transponder. Other types of tags have a local power source such as a battery and may operate at hundreds of meters from the reader.

RFID tags are used in a variety of environments, such as in health care, retail or commercial spaces, and industrial warehouses. In a healthcare environment, such as a hospital or clinic, the environment can include a variety of information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). These systems may store a variety of information such as patient medication orders, medical histories, imaging data, test results, diagnosis information, management information, and/or scheduling information. A retail or commercial space can also include a variety of information systems, such as a point-of-sale system, a payment information processing system, an inventory management system, and other such systems. These systems may also store a variety of information such as inventory types and amounts, how long a given inventory item has been displayed, how often a given inventory item has been sold, and other such information.

The effectiveness of a healthcare system can be determined by the interaction between the healthcare resources. Adverse events that occur in hospitals, such as hospital-acquired infections, lost or missing assets, etc., result in patient harm, increased recovery time, loss of a hospital's and its staffs capacity to serve, unreimbursed healthcare costs, and, generally, increased healthcare costs. One of the main causes of these events is non-adherence to protocols. Protocols can refer to a series of preferred or prescribed tasks that (1) have been proven to reduce adverse events and (2) effect a desired elimination of activities, practices, or patterns that create harm or inefficiency. Example uses of such protocols are for hand washing, fall prevention, rounding, pain management, sleep improvement and physical therapy.

Similarly, the effectiveness of a retail space can be determined by how often inventory items sell or whether a given portion of the retail space is being frequented by customers. Increases in customer visits to a particular location in a store may indicate that customers have an interest in items being sold in that particular location, while decreases in customer visits to other parts of a store may indicate that customers are no longer interested in the items being sold in that part of the store. Thus, locations in a store experiencing a decrease in customer visits impact profitability as the items in those locations are less likely to be sold.

BRIEF DESCRIPTION OF THE DRAWINGS

Various ones of the appended drawings merely illustrate example embodiments of the present disclosure and cannot be considered as limiting its scope.

Figure 1:
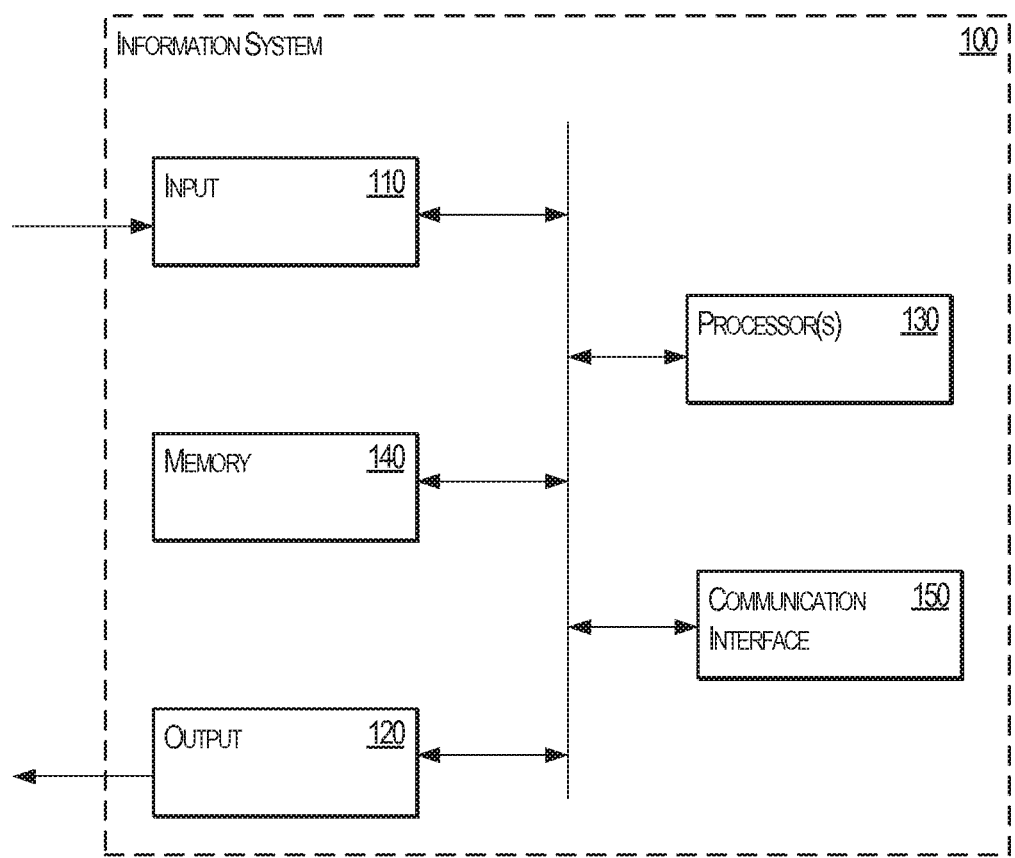
FIG. 1 is a block diagram of an information system, according to an example embodiment.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Certain examples of the disclosed technology improve proximity detection and location tracking with a mobile wireless bridge. The disclosed systems and methods include one or more beacon tags positioned within an environment, such as a hospital room, retail space, industrial environment, or other such environment, and that transmit beacon messages. In one embodiment, the beacon messages are transmitted at fixed time intervals. In alternative embodiments, the beacon messages are transmitted at variable time intervals or as a single instance.

The beacon messages are received by a mobile wireless bridge platform that listens for low power Bluetooth Low Energy (BLE) beacon messages and connects to a Wi-Fi infrastructure. An example of Bluetooth Low Energy is Bluetooth® Smart, which one of ordinary skill in the art will recognize as a power-friendly version of Bluetooth wireless technology.

The mobile wireless bridge platform (sometimes referred to herein as a "badge" or "beacon badge") processes the received beacon messages and communicates information obtained from the beacon messages to a real-time location services (RTLS) server via the Wi-Fi infrastructure (e.g., a wireless network). The RTLS server aggregates the information received from one or more badges over an interval of time and reports the aggregated information. In various embodiments, the reports may include text and/or graphics, such as charts, graphs, tables, etc.

The disclosed real-time location services can improve the efficiency of a working environment, such as patient workflow in a hospital environment, through proximity detection and location tracking. Location tracking can be used to locate assets (e.g., intravenous (IV) pumps, telemetry units, wheelchairs, etc.) within the hospital. For example, location tracking can be used to locate a "lost" or "missing" IV pump within a patient's room. Proximity detection facilitates an improved understanding of how interactions occur during the patient workflow. For example, based on the proximity to a soap dispenser, a user (e.g., a system administrator) can determine whether a caretaker washed his or her hands prior to interacting with a patient.

In another environment, such as a retail space, the disclosed real-time services can improve profitability and customer interactions by monitoring the sale of inventory and locations that customers tend to visit more frequently. For example, based on whether a location in a store is visited more or less frequently, the owner of the store can make adjustments in the inventory that are located at the location, such as by changing the inventory at the location or by increasing the amount of inventory at the location.

The technical effect of the disclosed RTLS system is that it facilitates improved proximity detection and location tracking by creating a tracking network within an environment using an existing network infrastructure, such as a wireless network infrastructure. Beacon tags are installed throughout a location or building. For example, beacon tags can be affixed to stationary and mobile assets such as hospital beds, IV pumps, soap dispensers, clothing, toys, kitchenwares, automobile accessories, industrial tools, or other such items. Beacon tags may also be included in disposable patient tags provided to the patient upon admission of a hospital stay.

Beacon tags are low-cost, low-power transmitters of beacons. A beacon (sometimes referred to herein as a "beacon message") includes information about the beacon tag such as a unique identifier and location information. In one embodiment, the beacon tags broadcast beacon messages at fixed time intervals. In alternative embodiments, the beacon messages are transmitted at variable time intervals or as a single instance.

Beacon badges are mobile wireless bridges that facilitate mobile tracking by "listening" and receiving the beacon messages. The beacon badge includes a BLE chip to receive connection-less beacon messages from beacon tags and a wireless transceiver to establish a connection with an RTLS server. The beacon badges may be worn or transported by an employee, such as a doctor, retail clerk, equipment operator, or other such employee. As the employee moves about the environment, the beacon badge passively collects beacon messages and communicates beacon packets to an RTLS server at the backend of the system.

In some examples, the beacon badge collects a number (e.g., a predetermined number) of beacon messages or waits a given amount of time prior to communicating the beacon packets. In some examples, the beacon badge communicates a beacon packet as a beacon message is received. A beacon packet includes information received from the beacon message such as a unique identifier of the source beacon tag and a spatial location of the source beacon tag. The beacon badge also includes, in the beacon packet, a timestamp identifying when the beacon message was received by the beacon badge and a received signal strength indication (RSSI) value (e.g., a power ratio in decibels of the measured power to one milli-watt (dBm)).

Example beacon badges disclosed herein include a proximity engine to process the beacon messages and determine a distance from the source of the beacon messages (e.g., the beacon tag that broadcasts the corresponding beacon message). For example, a hospital room may include a first beacon tag affixed to a door, a second beacon tag affixed to an infusion pump, a third beacon tag affixed to a bed, and a fourth beacon tag included in a patient tag (e.g., a disposable bracelet including patient identification information such as name, sex, date of birth information). As the caregiver moves about the hospital room, the beacon badge may receive beacon messages from each of the beacon tags. The proximity tag can determine the RSSI value for each of the beacon messages and associate an RSSI value with a respective beacon tag.

In some examples, the proximity engine determines which beacon tags are proximate (e.g., near or closely located) to the beacon badge. For example, the proximity engine can compare the RSSI value of a beacon message to a threshold and if the RSSI value satisfies the threshold (e.g., the RSSI value is greater than a threshold value), the proximity engine identifies the source beacon tag as proximate to the beacon badge. In some examples, the proximity engine discards beacon messages that are not proximate to the beacon badge.

Example systems and methods disclosed herein include an RTLS server that monitors and/or reports tracking location and interactions between people and assets in an environment. For example, the RTLS server aggregates beacon packets from the one or more beacon badges included in the environment (e.g., the hospital). The RTLS server communicates with the beacon badges via a wireless network, such as a wireless local area network, a wireless wide area network, or a combination thereof.

In one embodiment, the disclosed wireless network bridge, beacon badges, and beacon tags are used in the processing of health information. While the following description is directed to the processing of health information, one of ordinary skill in the art will recognize that the described systems and methods can be adapted for other environments and/or infrastructures. Thus, in the following description of employing the disclosed systems and methods in the processing of health information, such description should be understood as not excluding other applications of such systems and methods.

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive PHI and employee information between diverse locations to improve hospital operational efficiency in an operational environment typically having a chaotic-driven demand by patients for hospital services. In certain examples, patient-identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides users with a plurality of information and functionality including medical devices, electronic records, access portals, pay for performance (P4P), chronic disease models, clinical health information exchange/regional health information organization (HIE/RHIO), home health, and/or enterprise pharmaceutical studies, for example.

Interconnection of multiple data sources facilitates engagement of all relevant members of a patient's care team and improves the administrative and management burden on the patient for managing his or her care. Particularly, interconnecting the patient's electronic medical record and/or other medical data improves patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced service-oriented architecture (SOA) with a modern technology stack provides robust interoperability, reliability, and performance. An example SOA can include a three-fold interoperability strategy having a central repository (e.g., a central repository built from Health Level Seven (HL7) transactions), services for working in federated environments, and visual integration with third-party applications. Certain examples provide portable content enabling "plug 'n play" content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time, assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

FIG. 1 is a block diagram of an information system 100, according to an example embodiment. Where the information system 100 is implemented within a healthcare organization, the information system 100 incorporates a variety of systems and processes including, but not limited to, image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

In other environments, such as a retail storefront or industrial center, the information system 100 includes additional or alternative systems and processes, such as a customer relationship management systems, inventory management systems, point-of-sale systems, record management systems, employee management systems, payroll management systems, quality and document control systems, and other such systems or combination of systems.

As illustrated in FIG. 1, the information system 100 includes an input 110, an output 120, one or more processors 130, a memory 140, and a communication interface 150. The components of example system 100 can be integrated in one device or distributed over two or more devices.

The input 110 may include a keyboard, a touch-screen, a mouse, a trackball, a track pad, optical barcode recognition, voice command, etc. or combination thereof used to communicate an instruction or data to system 100. The input 110 may include an interface between systems, between user(s) and system 100, etc.

In one embodiment, the output 120 provides a display generated by processor 130 for visual illustration on a monitor or the like. The display can be in the form of a network interface or graphic user interface (GUI) to exchange data, instructions, or illustrations on a computing device via communication interface 150, for example. Examples of output 120 include a monitor (e.g., liquid crystal display (LCD), plasma display, cathode ray tube (CRT), etc.), light emitting diodes (LEDs), a touch-screen, a printer, a speaker, or other conventional display device or combination thereof.

The one or more processors 130 include hardware and/or software for configuring the hardware to execute one or more tasks and/or implement a particular system configuration. The one or more processors 130 process data received at input 110 and generate a result that can be provided to one or more of output 120, memory 140, and/or communication interface 150. For example, and in one embodiment, the one or more processors 130 receive user annotation provided via input 110 with respect to an image displayed via output 120 and generate a report associated with the image based on the annotation. As another example, the one or more processors 130 process updated patient information obtained via input 110 to provide an updated patient record to an EMR via communication interface 150. As yet a further example, the one or more processors 130 process inventory quantities received via input 110 and generate a report associated with the received inventory levels via output 120.

The memory 140 may include a relational database, an object-oriented database, a data dictionary, a clinical data repository, a data warehouse, a data mart, a vendor neutral archive, an enterprise archive, etc. In one embodiment, the memory 140 stores images, patient data, best practices, clinical knowledge, analytics, reports, etc. In another embodiment, the memory 140 stores employee records, inventory types and quantities, payroll information, and other retail information. The memory 140 stores data and/or instructions accessible by the processor 130. In certain examples, memory 140 is accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 stores information securely. For example, a patient's data can be encrypted with a unique patient-owned key at the source of the data. The data is then uploaded to memory 140. Privacy with respect to the patient data is maintained as the memory 140 may not store unencrypted patient data. The patient's data can be downloaded and decrypted locally with the encryption key.

Where the information system 100 is implemented for healthcare, the memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

The communication interface 150 facilitates transmission of electronic data within and/or among one or more systems. Communication via communication interface 150 can be implemented using one or more protocols. Where the information system 100 is implemented for healthcare management, communication via communication interface 150 occurs according to one or more standards (e.g., Digital Imaging and Communications in Medicine (DICOM), Health Level Seven (HL7), ANSI X12N, etc.). However, other standards may also be used depending on the context in which the information system 100 is implemented.

The communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using one or more communication protocols (e.g., BLUETOOTH™, USB 2.0, USB 3.0, etc.) or combination of protocols.

In certain examples, a Web-based portal may be used to facilitate access to information, such as patient care, practice management, employee information, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

Figure 2:
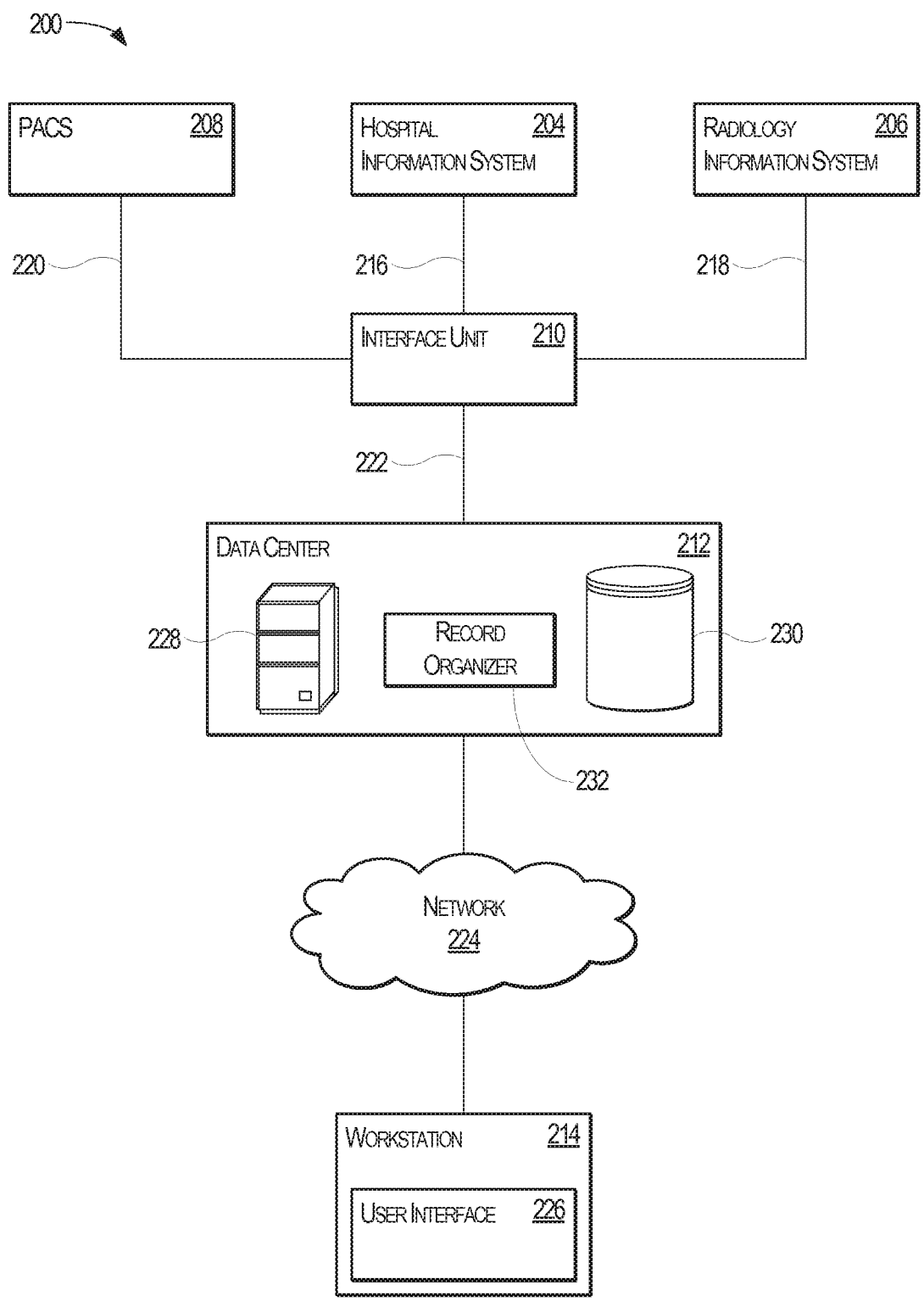
FIG. 2 is a block diagram of an information infrastructure, according to an example embodiment.

FIG. 2 is a block diagram of an information infrastructure 200, according to an example embodiment. In one embodiment, the information infrastructure 200 is implemented as a healthcare-oriented system. In this embodiment, the information infrastructure 200 includes an HIS 204, an RIS 206, a PACS 208, an interface unit 210, a data center 212, and a workstation 214.

In one embodiment, HIS 204, RIS 206, and PACS 208 are housed in a healthcare facility and locally archived. However, in other implementations, HIS 204, RIS 206, and/or PACS 208 may be housed within one or more other suitable locations. In alternative embodiments, one or more of PACS 208, RIS 206, HIS 204, are implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together.

In yet other embodiments, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination. One or more of the HIS 204, RIS 206, and/or PACS 208 can communicate with equipment and system(s) in an operating room, patient room, etc., to track activity, correlate information, generate reports and/or next actions, and the like.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation 214 to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a wide area network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless local area network, and/or a wired or wireless wide area network. In some examples, interface unit 210 also includes a broker (e.g., a Mitra Imaging's PACS broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. In some embodiments, such as when different formats of the received information are incompatible, interface unit 210 translates or reformats (e.g., into Structured Query Language ("SQL") or standard text) the medical information, such as medical reports, to be stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc.

In one embodiment, workstation 214 implements a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

The data center 212 stores information such as images, data, medical reports, and/or, more generally, patient medical records. In addition, data center 212 acts as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In various embodiments, the data center 212 is spatially distant from HIS 204, RIS 206, and/or PACS 208.

In one embodiment, the data center 212 includes a server 228, a database 230, and a record organizer 232. Server 228 receives, processes, and conveys information to and from the components of healthcare system 200. Database 230 stores the medical information described herein and provides access thereto. The record organizer 232 manages patient medical histories, assists in procedure scheduling, and engages in other operations directed to organizing one or more patient records.

The healthcare system 200 may be implemented as a cloud-based clinical information system. A cloud-based clinical information system enables healthcare entities (e.g., patients, clinicians, sites, groups, communities, and/or other entities) to share information via web-based applications, cloud storage and cloud services. For example, a cloud-based clinical information system enables a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network 224, for example. In certain examples, all or part of system 200 can also be provided via a platform as a service (PaaS), infrastructure as a service (IaaS), etc. For example, system 200 can be implemented as a cloud-delivered mobile computing integration platform as a service. A set of consumer-facing Web-based, mobile, and/or other applications enable users to interact with the PaaS, for example.

While FIG. 2 illustrates interconnections between systems and data, the disclosed systems and methods also apply within the context of the internet of things. The internet of things (also referred to as the "Industrial Internet") relates to an interconnection between a device that can use an Internet connection to talk with other devices on the network 224. Using the connection, devices can communicate to trigger events/actions (e.g., changing temperature, turning on/off, providing a status, etc.). In certain examples, machines can be merged with "big data" to improve efficiency and operations and provide improved data mining.

"Big data" generally refers to a collection of data so large and complex that it becomes difficult to process using traditional data processing tools/methods. Challenges associated with a large data set include data capture, sorting, storage, search, transfer, analysis, and visualization. A trend toward larger data sets is due, at least in part, to additional information derivable from analysis of a single large set of data, rather than analysis of a plurality of separate, smaller data sets. By analyzing a single large data set, correlations can be found in the data, and data quality can be evaluated.

Figure 3:
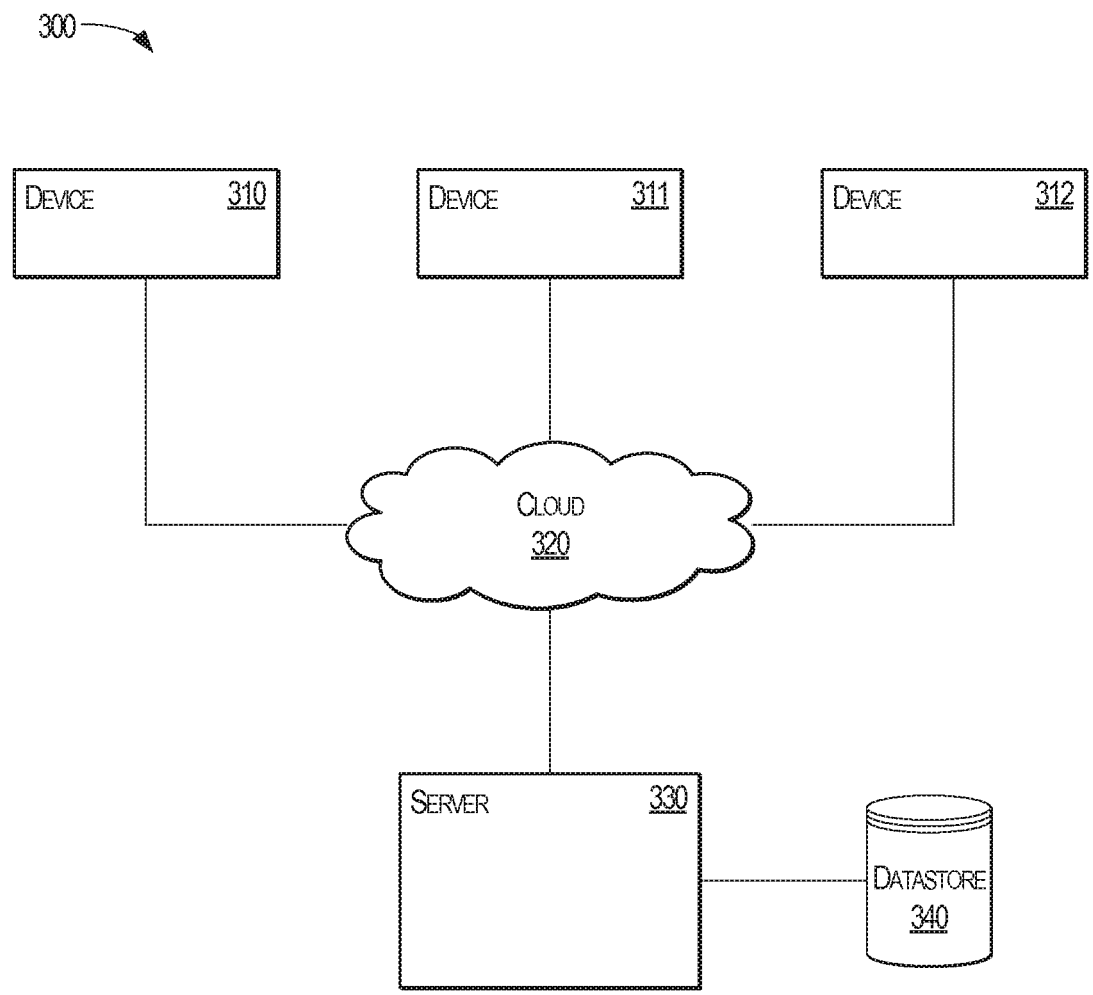
FIG. 3 is an industrial Internet configuration, according to an example embodiment.

FIG. 3 depicts an industrial Internet configuration 300, according to an example embodiment. As with FIG. 2, the industrial Internet configuration 300 is directed to a healthcare-oriented implementation. However, the industrial Internet configuration 300 may be configured to other environments as well, such as a retail store, a factory floor, a construction site, or other such environment. In one embodiment, the configuration 300 includes a plurality of devices 310-312 that access a network cloud 320, which connects the devices 310-312 with a server 330 and associated data store 340. In the context of healthcare, devices 310-312 include such devices as pumps, electrocardiographs, inhalers, contact lenses, medicine containers, and other such devices. Other examples of devices 310-312 include printers, RFID tags, RFID readers, scanners, point-of-sale machines, credit card readers, and other such devices. Furthermore, devices 310-312 may also include systems, machines, servers, desktop computers, laptop computers, or combinations of such devices.

In this manner, devices 310-312 become "intelligent" as a network 224 with advanced sensors, controls, analytical-based decision support and hosting software applications. Using such an infrastructure, advanced analytics can be provided to associated data. The analytics combines physics-based analytics, predictive algorithms, automation, and deep domain expertise. Via network cloud 320, devices 310-312, and associated people, can be connected to support more intelligent design, operations, maintenance, and higher server quality and safety, for example.

Using the industrial Internet configuration 300, for example, a proprietary machine data stream can be extracted from a device 310. Machine-based algorithms and data analysis are applied to the extracted data. Data visualization of the extracted data can be remote, centralized, etc. The extracted data is then shared with authorized users, and any gathered and/or gleaned intelligence can be provided back to the devices 310-312.

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

The foregoing systems and methods may be applied in the context of a clinical workflow. Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information.

The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In various embodiments, a medical exam conducted on a patient can involve review by a healthcare practitioner, such as a radiologist, to obtain, for example, diagnostic information from the exam. In a hospital setting, medical exams can be ordered for a plurality of patients, all of which may be reviewed by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

The foregoing systems and methods may be deployed to provide real-time location services. Real-time location services (RTLS) facilitate tracking people and assets in an industrial setting, such as a hospital. In one embodiment, an RTLS system is implemented to capture location and proximity information and interactions information from beacon tags installed throughout a hospital. In this embodiment, beacon tags are installed, for example, in the hallways, rooms, equipment, patient wristbands, and in other such locations. In another embodiment, an RTLS system is implemented to capture such location and proximity information from beacon tags installed in a retail store. In this alternative embodiment, the beacon tags are installed, for example, at a point-of-sale machine, within security tags affixed to one or more items, in various aisles, near particular types of inventory, and in other such locations.

Where the beacon tags are installed in a hospital, a caregiver (e.g., a doctor, a nurse, etc.) attaches a beacon badge to themselves (e.g., via a lanyard, a pocket clip, etc.), and as the caregiver performs their duties, the example RTLS system passively captures the location/proximity information and interactions information from the beacon tags. The location/proximity information and interactions information is processed by the beacon badge and sent, via a wireless infrastructure, to a RTLS server. Application event(s) (e.g., interactions between a caregiver and a patient, room level proximity detection, etc.) are generated based on the received location/proximity information and interaction information. In some examples, a beacon badge may be placed on a bed or other asset for which location/proximity information is to be collected between beacon tags and the asset.

In some examples, a beacon badge may be coupled to an extension that facilitates extended battery life for the beacon badge. For example, a hub module is a module with an external power source (e.g., an AC/DC power connection) that can be coupled to a beacon badge via a module connector on the beacon badge and a badge connection on the hub module. The external power source enables the beacon badge to pull power from the hub module rather than its own battery, thereby increasing the battery life and capabilities of the beacon badge. In some examples, a hub module is placed on stationary (or near stationary) equipment, such as a bed, to detect when a patient interacts with the stationary equipment (e.g., moves from the bed). In some examples, the hub module may include one or more sensors to detect additional events. For example, a hub module may be placed on a soap dispenser and include sensors to detect when the soap dispenser performs a dispense event.

The example RTLS system disclosed herein also includes one or more dock modules located throughout an environment. Example dock modules are utilized to charge one or more beacon badges. For example, when a caregiver goes off-duty, the caregiver may dock (e.g., couple) their beacon badge with the dock module, which includes an external power source (e.g., an AC/DC power connection) to charge the beacon badge.

In some examples, the beacon badge is assigned to a caregiver over a period of time (e.g., six months, one year, etc.). In some examples, the beacon badge is assigned to a caregiver as needed. For example, rather than using the same beacon badge during each hospital shift, the caregiver may be assigned a different beacon badge at the start of their shift. In some such examples, the dock module may include additional components to monitor and/or track beacon badge check-in/check-out, or example, the dock module may log when a beacon badge is removed from and/or coupled to the dock module. In some such examples, the dock module includes an identification component enabling a caregiver to identify themselves to the system via a unique identifier (e.g., a hospital identifier, a user identifier, etc.).

For example, at the beginning of a caregiver's shift, the caregiver may identify themselves to the dock module via a barcode scanner, an RFID reader, near field communication (NFC) reader, a BLE reader, a touchpad, a touch screen interface, etc. of the identification component. When a caregiver is authenticated, the dock module assigns a beacon badge to the caregiver. In some such examples, the dock module and/or the beacon badge may include LEDs to indicate which beacon badge coupled to the dock module is assigned to the caregiver. Additionally or alternatively, the dock module may include a locking mechanism that unlocks a beacon badge when assigned to the caregiver. In some examples, the dock module monitors the charge level (e.g., power level) of the docked beacon badges and assigns a beacon badge to the caregiver based on the charge level. For example, the dock module can determine the beacon badge with the highest charge level and assign that beacon badge first. When a beacon badge is returned to the dock module (e.g., at the end of a shift, when the beacon badge battery reaches a critical or shutdown level, etc.), the dock module disassociates the beacon badge from the caregiver. The dock module may assign the beacon badge to the same caregiver and/or a different caregiver during subsequent use of the beacon badge. The beacon badge can then be charged while it awaits its next use. In some such examples, a returning of the beacon badge to the dock module for recharging triggers a disassociation or unassignment of the beacon badge to the caregiver.

Figure 4:
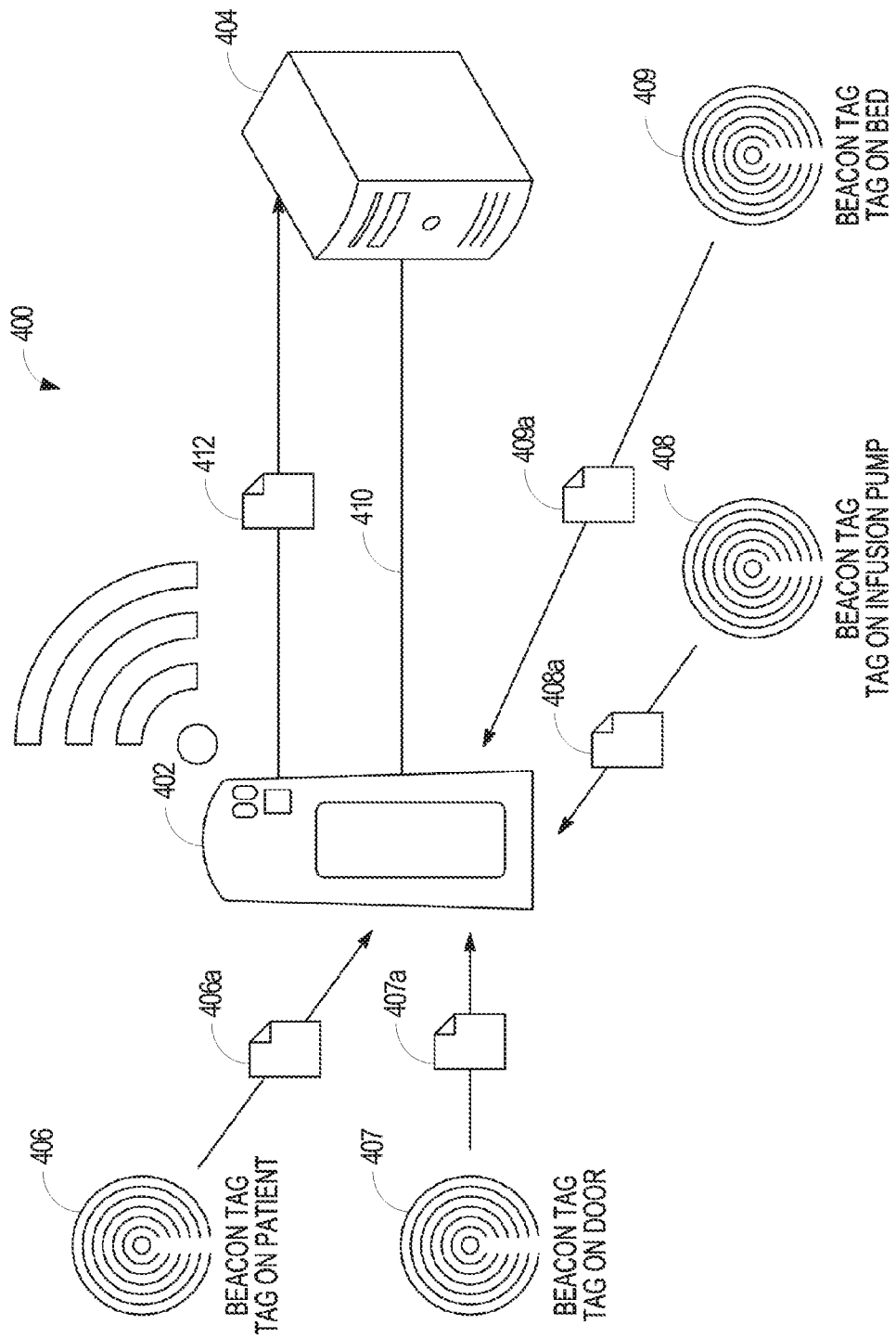
FIG. 4 is a block diagram illustrating an environment that facilitates proximity detection and location tracking using a mobile wireless bridge, according to an example embodiment.

FIG. 4 is a block diagram illustrating an environment 400 that facilitates proximity detection and location tracking using a mobile wireless bridge, according to an example embodiment. The environment 400 of FIG. 4 includes a mobile wireless bridge 402 (e.g., a beacon badge), an example real-time locations services (RTLS) server 404 and example beacon tags 406-409. In the illustrated example of FIG. 4, the RTLS server 404 is a server and/or database that collects and/or receives beacon packets related to proximity/location information and interactions information. In some examples, the RTLS server 404 is implemented using multiple devices. For example, the RTLS server 404 may include disk arrays or multiple workstations 214 (e.g., desktop computers, workstation servers, laptops, etc.) in communication with one another.

In the illustrated example, the beacon badge 402 is in communication with the RTLS server 404 via one or more wireless networks represented by network 410. Example network 410 may be implemented using any suitable wireless network(s) including, for example, one or more data busses, one or more wireless local area networks (LANs), one or more cellular networks, the Internet, etc. As used herein, the phrase "in communication," including variances thereof (e.g., communicates, in communication with, etc.), encompasses direct communication and/or indirect communication through one or more intermediary components and does not require direct physical (e.g., wired) communication and/or constant communication, but rather additionally includes communication at periodic or aperiodic intervals, as well as one-time events.

In the illustrated example of FIG. 4, the mobile wireless bridge 402 is a beacon badge that receives one or more example beacon messages 406a-409a from the corresponding source beacon tags 406-409. For example, the beacon tag 406 broadcasts the beacon message 406a, the beacon tag 407 broadcasts the beacon message 407a, the beacon tag 408 broadcasts the beacon message 408a and the beacon tag 409 broadcasts the beacon message 409a. The example beacon tags 406-409 broadcast the corresponding beacon messages 406a-409a periodically (e.g., once a second, once a minute, once every ten minutes, etc.). In other examples, the beacon tags 406-409 may broadcast the corresponding beacon messages 406a-409a at different intervals. For example, stationary assets such as a bed or a door may broadcast beacon messages 406a-409a less frequently than mobile assets such as merchandise, medical devices (e.g., IV pumps, an infusion pump, etc.) or other such mobile assets.

In the illustrated example, the beacon messages 406a-409a include identification information for the source beacon tag 406-409. For example, the beacon message 406a may include a unique identifier of the beacon tag 406 and location information for the beacon tag 406. In some examples, the location information may be spatial coordinates (e.g., longitude and latitude coordinates) and/or general location identifiers (e.g., operating room #1, patient room 312, infusion pump #8, men's dressing room, aisle number five, women's dressing room, etc.).

In the illustrated example, the beacon tags 406-409 are implemented using low-power BLE transmitters and include a single coin-cell battery. In some examples, the single coin-cell battery provides power to the beacon tags 406-409 for two or more years. The beacon tags 406-409 are installed throughout an environment. For example, where the environment 400 is a hospital or other healthcare facility, the example beacon tag 406 is located on a patient (e.g., inserted within a patient tag), the example beacon tag 407 is located on a door, the example beacon tag 408 is located on an infusion pump and the example beacon tag 409 is located on a bed. As another example, where the environment 400 is a retail store or other commercial establishment, the example beacon tag 406 is located in the men's changing room, the example beacon tag 407 is located in the women's changing room, the example beacon tag 408 is located near men's clothing, and the example beacon tag 409 is located near the women's clothing.

In the environment 400, accuracy of the location/proximity information and interaction information can be increased or decreased based on adding or reducing the number of beacon tags placed in the environment 400.

In the illustrated example, the beacon badge 402 is worn by a hospital caregiver such as a doctor, a nurse, etc. In response to receiving beacon messages (e.g., one or more of the example beacon messages 406a-409a), the beacon badge 402 generates an example beacon packet 412. The example beacon packet 412 includes information obtained from the beacon messages 406a-409a, a timestamp indicating when the respective beacon message was received, and an RSSI value. However, other information may be included in the beacon messages 406a-409a and/or the beacon packet 412. Periodically and/or aperiodically, the beacon badge 402 transmits the location/proximity information and interaction information (e.g., the beacon packet 412) to the RTLS server 404.

Figure 5:
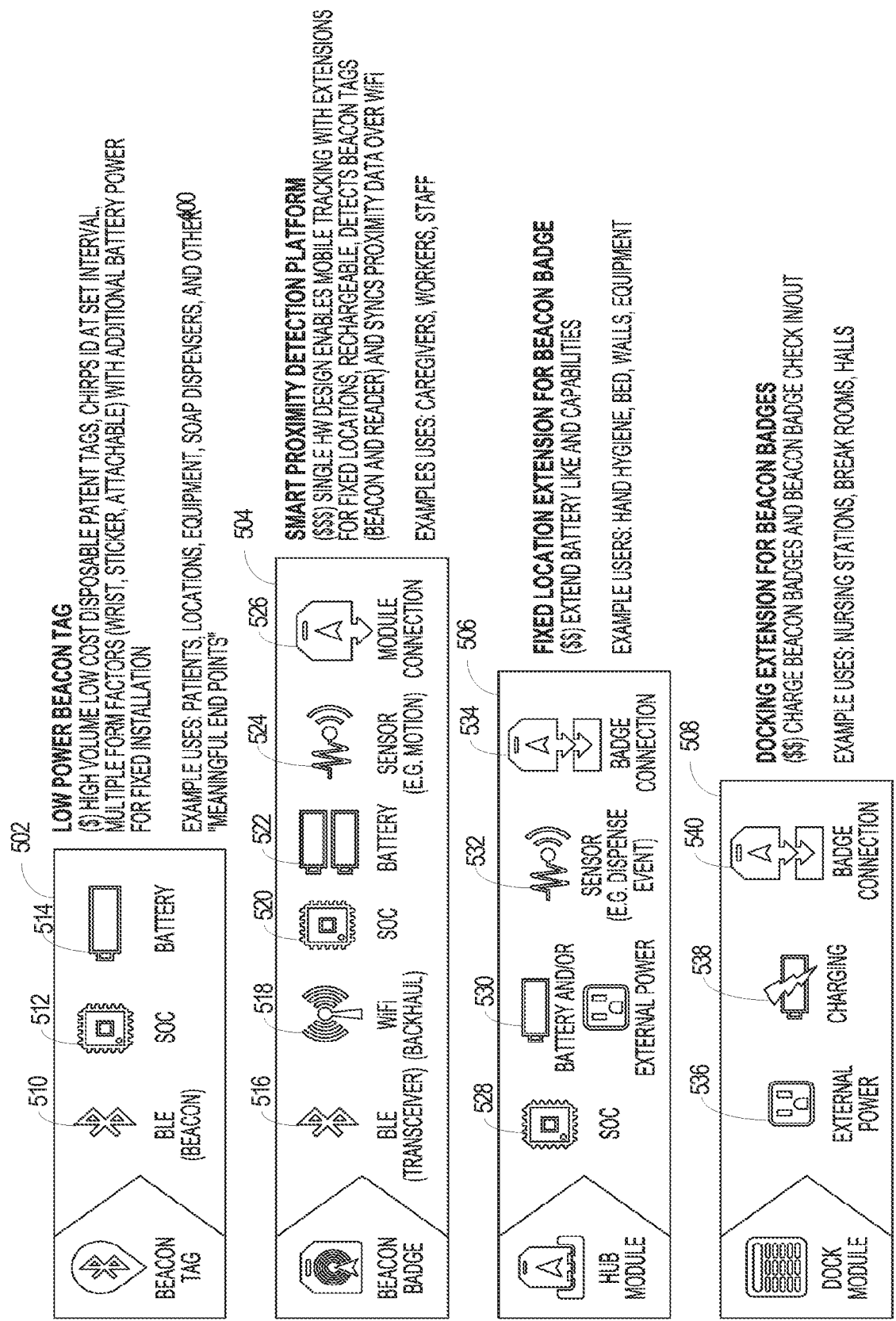
FIG. 5 illustrates various components included in a beacon tag, a beacon badge, as hub module and a dock module, according to various example embodiments.

FIG. 5 illustrates various components included in an example beacon tag 502, an example beacon badge 504, an example hub module 506 and example dock module 508. For example, the beacon tag 502 includes one or more BLE chips (labeled "Beacon") 510 to transmit beacon messages 406a-409a, one or more power sources 514 (e.g., one or more coin-cell batteries) and a system-on-a-chip (SOC) 512 to manage the one or more BLE chips 510 and the one or more power sources 514. The example beacon badge 504 includes one or more BLE chips 516 (labeled "transceiver") to receive beacon messages 406a-409a, one or more Wi-Fi chips 518 to communicate with a wireless network (e.g., the example network 410 (FIG. 4)), one or more power sources (e.g., one or more batteries) 522, one or more sensors 524 (e.g., a motion sensor, an accelerometer, a gyroscope, etc.) and a system-on-a-chip (SOC) 520 to manage the one or more BLE chips 516, the one or more Wi-Fi chips 518, the one or more power sources 522 and the one or more sensors 524. The example beacon badge 504 also includes an example module connector 526 to connect the beacon badge 504 to the example hub module 506 and/or the dock module 508.

In the illustrated example, the beacon badge 504 is connectable to the example hub module 506. The connection between the beacon badge 504 and the hub module 506 may include a mechanical connection, an electrical connection, or combinations thereof. In the illustrated example, the hub module 506 may be used to track asset interactions with fixed locations. In a healthcare environment, examples of fixed locations include soap dispensers, beds, walls, equipment, etc. In other environments, such as a retail environment, fixed locations may include wall sconces, light fixtures, mirrors, shelving, and other such fixed locations.

The hub module 506 may be leveraged to identify particular locations. As an example, the beacon badge 504 may be coupled, via a badge connection 534, to a hub module 506 placed on an entrance to a restricted area to identify when a person wearing a beacon tag 502 enters (or approaches) the restricted area. In one embodiment, the hub module 506 includes a system-on-a-chip (SOC) 528 to manage components of the hub module 506, one or more power sources 530 (e.g., one or more batteries and an external power source (e.g., an AC/DC connection)) to extend the battery life and capabilities of the beacon badge 504, one or more sensors 532 communicatively coupled to the SOC 528, and a badge connection 534 for connecting the beacon badge 504 to the hub module 506.

In the illustrated example, the beacon badge 504 may be connectable (e.g., mechanically coupled, electronically coupled, etc.) to the example dock module 508. In the illustrated example, the dock module 508 may be used to charge one or more beacon badges 504. Accordingly, and in one embodiment, the dock module 508 includes an external power connector 536 (e.g., an AC connector), a charging indicator 538 to indicate whether the beacon badge 504 is charged or charging, and a badge connection 540 for connecting the beacon badge 504 to the dock module 508. In one embodiment, the dock module 508 is portable. For example, the dock module 508 may be placed throughout one or more environments, such as at cash registers, podiums, counters, nursing stations, break rooms, hallways, etc., and a caregiver may couple their beacon badge 504 to the dock module 508, via a badge connection 540, when they are off-duty.

Figure 6:
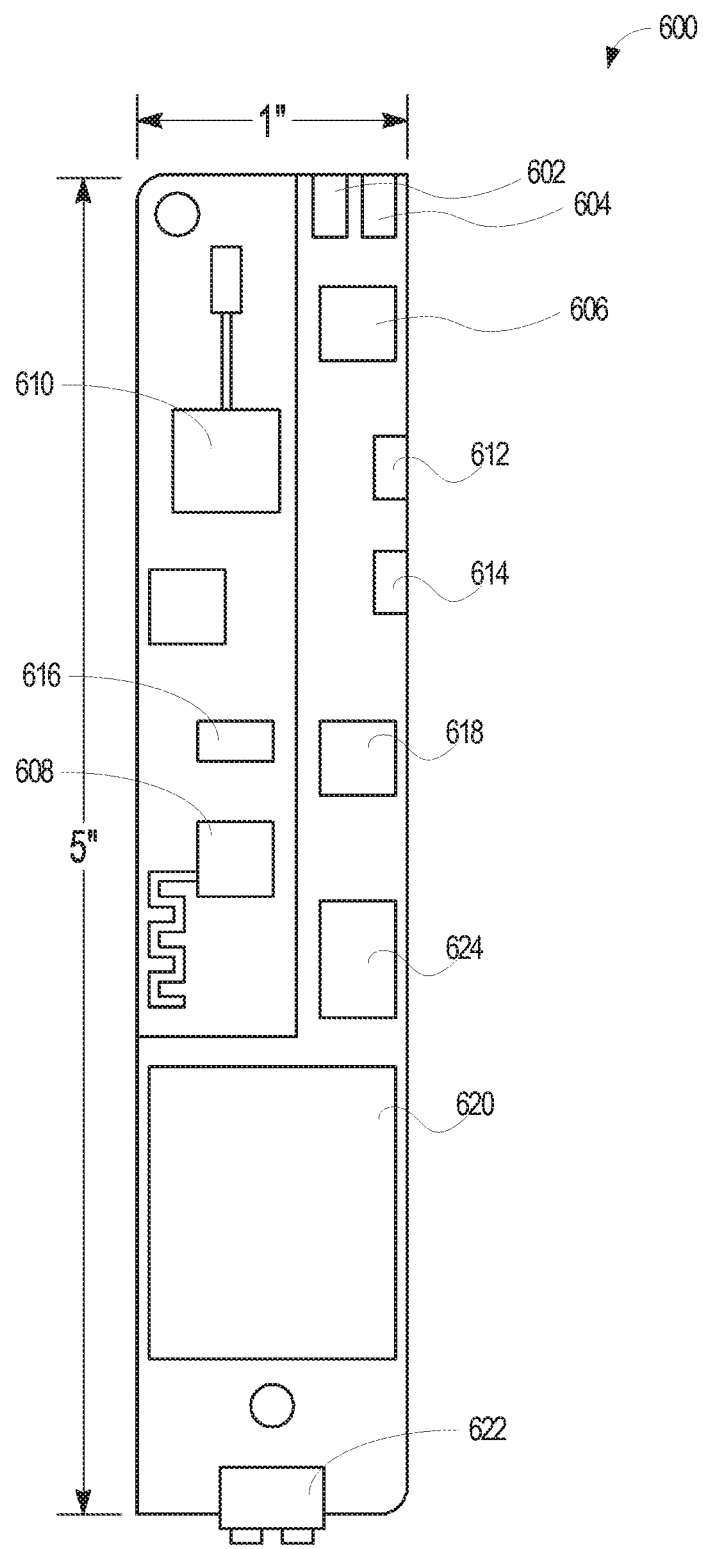
FIG. 6 illustrates a beacon badge, according to an example embodiment.

The beacon badge 504 may be deployed as a relatively small and portable electronic device. FIG. 6 illustrates a beacon badge 600, according to an example embodiment. In one embodiment, the beacon badge 600 has a dimension of one (1) inch wide by five (5) inches across. However, other dimensions are also possible. The example beacon badge 600 includes example light-emitting diodes (LEDs) 602-604 to indicate status information. For example, the LEDs 602-604 may indicate when the battery charge of the beacon badge 600 is low, when the beacon badge 600 is connected to the example RTLS server 404 (FIG. 4) and/or transmitting information (e.g., the example beacon packet 412 (FIG. 4)) via the wireless network 410 (FIG. 4), when the beacon badge 600 is receiving and/or processing beacon messages 406a-409a, etc.

The beacon badge 600 includes one or more transceivers for receiving information. In one embodiment, beacon badge 600 receives (e.g., collects, detects, captures, obtains, etc.) beacon messages 406a-409a via an IR sensor 606 and/or a BLE chip 608. The beacon badge 600 also includes a wireless network transceiver 610 to communicate beacon packets (e.g., the example beacon packet 412) to the RTLS server 404 via a wireless infrastructure, such as the network 410 of FIG. 4.

The beacon badge 600 also includes user-input controls (e.g., buttons) 612-614 to control the beacon badge 600. The example beacon badge 600 also includes a motion sensor 616 and an internal measurement unit (IMU) chip 618 (e.g., a gyroscope processor) to manage power utilization of the beacon badge 600. For example, the motion sensor 616 and/or IMU chip 618 may determine the beacon badge 600 is at rest (e.g., placed on a table) for a period and transition the beacon badge 600 from a normal power utilization state to a low-power utilization state (e.g., a sleep state). The motion sensor 616 and/or IMU chip 618 may transition the beacon badge 600 to a normal power utilization state when the beacon badge 600 is not at rest (e.g., moving with a caregiver). In some examples, transitioning the beacon badge 600 to the low-power utilization state may include deactivating (e.g., turning off) one or more of the transceivers, such as the IR sensor 606, the BLE chip 608, and/or the wireless transceiver 610, to conserve power.

The example beacon badge 600 further includes power charging circuitry 620 to manage charging the beacon badge 600 when connected to a power charging device, such as the hub module 506 (FIG. 5) and/or the dock module 508 (FIG. 5). The beacon badge 600 also includes an external connector 622, such as a micro USB connection, to couple the beacon badge 600 to the hub module 506 and/or the dock module 508.

The beacon badge 600 also includes a proximity engine 624 to manage received beacon messages (e.g., the example beacon messages 406a-409a (FIG. 4)). In one embodiment, the proximity engine 624 is implemented as firmware residing on machine-readable medium coupled to the beacon badge 600. Accordingly, the proximity engine 624 may be written in any suitable computer programming and/or computer scripting language. When a beacon message 406a-409a is received, the proximity engine 624 generates a beacon packet 412 to send to the RTLS server 404. For example, the proximity engine 624 records source beacon tag 502 identification information, such as a unique identifier and location information, from the received beacon message 406a-409a. In some examples, the proximity engine 624 appends a timestamp indicative of when the beacon message 406a-409a was received by the beacon badge 600. The proximity engine 624 may also determine an RSSI value indicative of the signal strength (e.g., power level) of the received beacon message 406a-409a. In some such examples, the proximity engine 624 also appends the RSSI value to the record for the received beacon message 406a-409a.

In some examples the proximity engine 624 uses the RSSI values to determine proximity of the beacon badge 600 to the source beacon tag 502. For example, if the RSSI value satisfies a proximity threshold (e.g., the RSSI value is at least a minimum value), the proximity engine 624 determines the source beacon tag 502 is a proximate beacon tag 502. In some such examples, the proximity engine 624 discards the received beacon message 406a-409a if the RSSI value did not satisfy the proximity threshold. Using the comparison results of the RSSI value and the proximity threshold, the proximity engine 624 filters beacon messages 406a-409a which may be received from source beacon tags 502 located within the environment but to which the beacon badge 600 is not proximate, such as when the beacon badge 600 is worn or carried by a person.

For example, in the context of a healthcare environment, a caregiver may be positioned in one corner of a patient room and the beacon badge 600 may receive a faint beacon message 406a-409a from a source beacon tag 502 positioned at the other corner of the patient room. In some examples, the proximity threshold may vary based on the beacon tag type and the asset on which the beacon tag 502 is placed. For example, the area within which a caregiver is considered to be proximate to a bed may be larger than the area within which a caregiver is considered to be proximate to a telemetry unit. In the illustrated example, the proximity engine 624 collects beacon messages 406a-409a over a period and periodically transmits beacon packets 412 to the RTLS server 404. Additionally or alternatively, the proximity engine 624 may generate and transmit a beacon packet 412 when a beacon message 406a-409a is received from a proximate source beacon tag 502.

Figure 7:
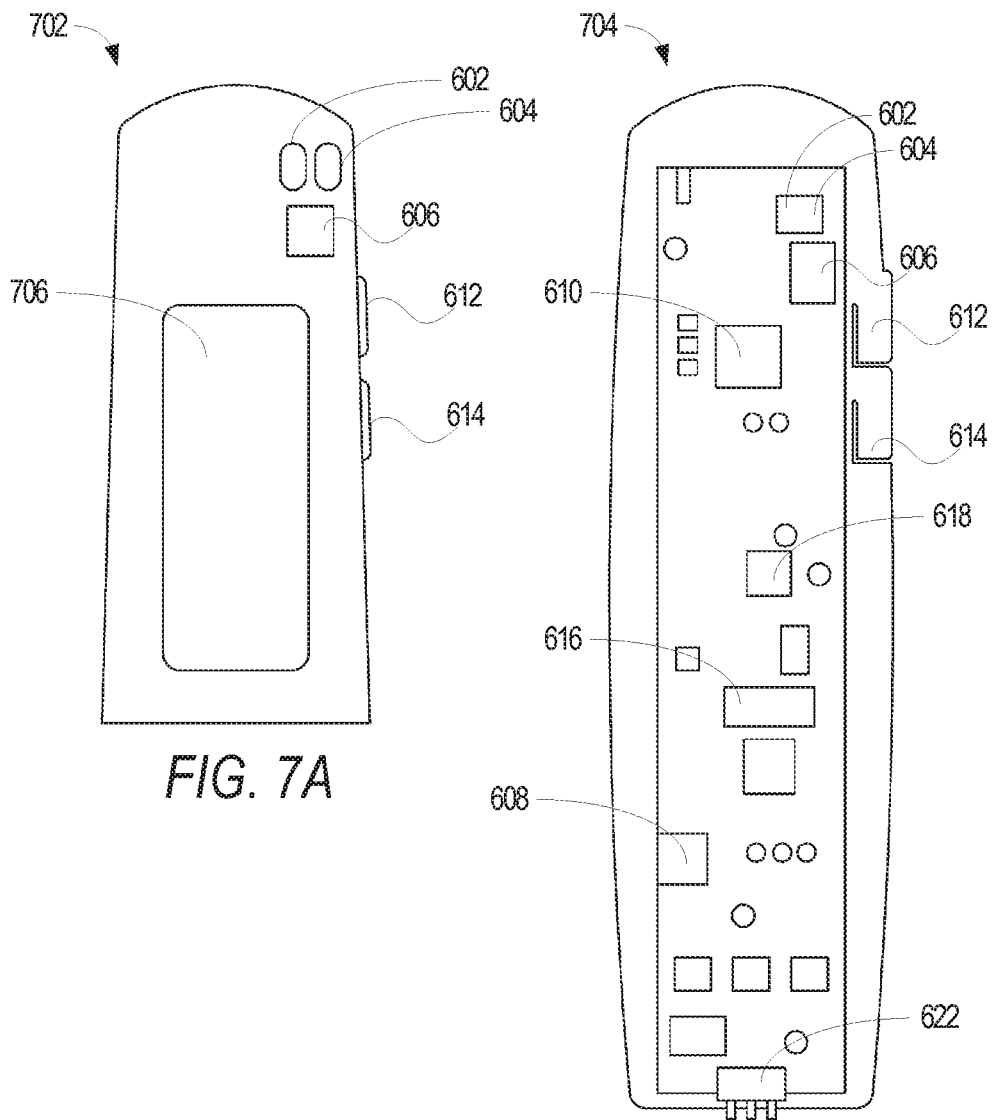
FIGS. 7A-7B illustrates additional details of the beacon badge, according to an example embodiment.

FIGS. 7A-7B illustrate additional details of the beacon badge 600, according to an example embodiment. In particular, FIG. 7A illustrates the outside build 702 of the beacon badge 600 and FIG. 7B illustrates a schematic view 704 of the beacon badge 600. The outside build 702 demonstrates the LEDs 602-604, the IR sensor 606 and the user-input controls 612-614 (e.g., depressible buttons). In one embodiment, the outside build 702 also comprises a front clip 706 for securing the beacon badge 600, such as by securing the beacon badge 600 to an article of clothing, merchandise, a chair, or other such item. For example, the font clip 706 can secure the beacon badge 600 to a doctor's coat pocket.

FIG. 7B illustrates example circuitry layout of the components of the beacon badge 600. In some instances, the example circuitry may differ from the components illustrated in FIG. 6; for example, the schematic view 704 does not include a proximity engine 624. In some such examples, the beacon badge 600 generates beacon packets 412 and sends them to the RTLS server 404 without filtering (e.g., discarding) the received beacon messages 406a-409a. The example RTLS server 404 may then filter the received beacon messages 406a-409a via a proximity engine 624 available to the RTLS server 404.

Figure 8:
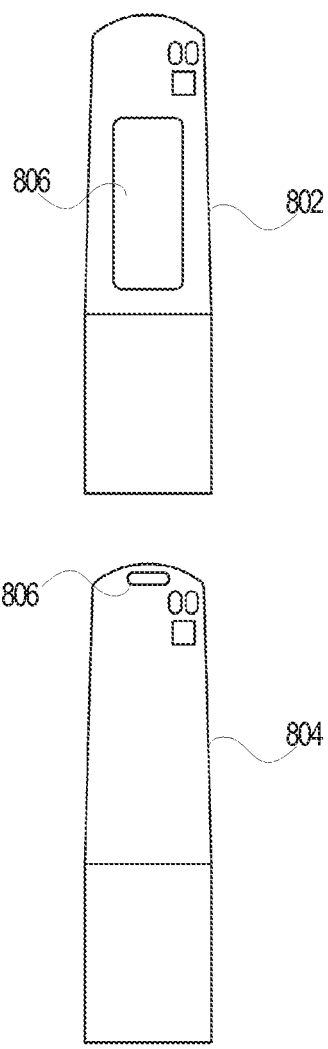
FIG. 8 illustrates alternative implementations to the beacon badge of FIG. 6, according to further embodiments.

FIG. 8 illustrates alternative implementations 802-804 to the beacon badge 600 of FIG. 6, according to further embodiments. In one implementation 802, the beacon badge 600 includes a front clip 806. In another implementation 804, the beacon badge includes lanyard receiver 806. One example of a lanyard receiver 806 is a hole formed within the surface of the beacon badge 600. As with the beacon badges 600 illustrated in FIG. 6 and FIGS. 7A-7B, the implementations 802-804 shown in FIG. 8 also include LEDs 602, 604, an IR sensor 606 and user-input controls 612-614.

Figure 9:
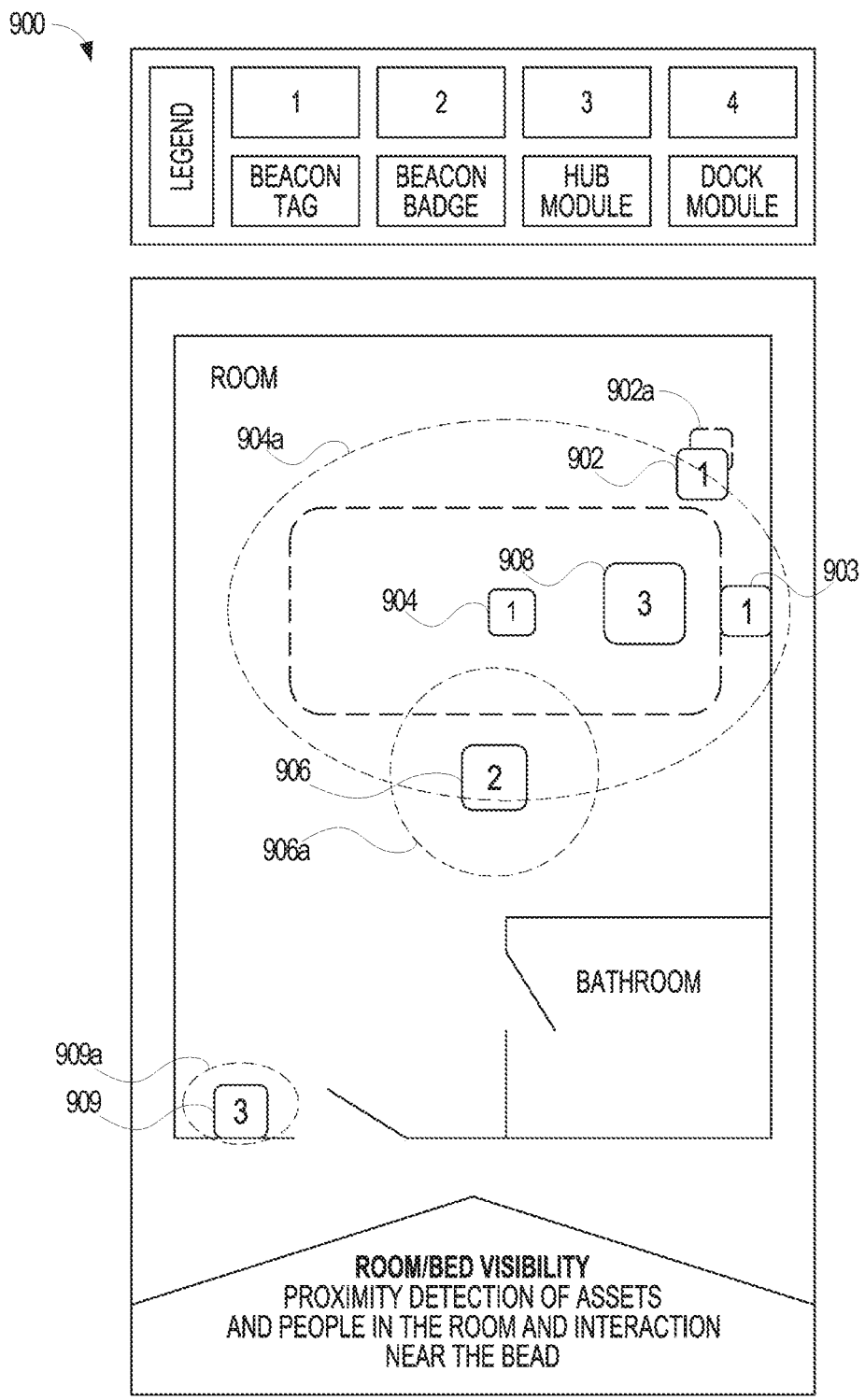
FIG. 9 illustrates an example environment to facilitate proximity detection and location tracking using a mobile wireless bridge, according to an example embodiment.

The beacon badge 600 illustrated in the foregoing figures may be used in a variety of environments. Accordingly, FIG. 9 illustrates an example environment 900 to facilitate proximity detection and location tracking using a mobile wireless bridge 402, according to an example embodiment. In one embodiment, the environment 900 is a healthcare facility. Thus, as shown in FIG. 9, the environment 900 includes a beacon tag 902 placed on equipment (e.g., an infusion pump, a telemetry unit, etc.), a beacon tag 903 placed at a location (e.g., against a wall) and a beacon tag 904 placed on a patient (e.g., via a patient tag). The environment 900 also includes a beacon badge 906 placed on a caregiver and hub modules 908, 909 placed on a bed and on a hand hygiene dispenser, respectively. In the illustrated example, each of the beacon tags 902-904, the beacon badge 906 and the hub modules 908, 909 are associated with a proximity area. The proximity area for a beacon tag 902-904 corresponds to the area around the beacon tag 902-904 in which the beacon tag 902-904 broadcasts its beacon messages 406a-409a and in which a received beacon message 406a-409a has an RSSI value that satisfies a proximity threshold. The proximity area for a beacon badge 906 corresponds to the area around the beacon badge 906 in which the caregiver may be considered to be interacting with an asset. The proximity area for a hub module 908, 909 corresponds to the area around the hub module 908, 909 in which an asset is considered to be proximate to the hub module 908, 909.

As shown in FIG. 9, the size of the proximity areas for the beacon tags 902-904, the beacon badge 906, and the hub modules 908-909 are different. For example, the proximity area 909a, corresponding to the area within which an asset is considered to be proximate to the hand hygiene dispenser, is less than the proximity area 904a, corresponding to the area within which a caregiver is considered to be interacting with an asset (e.g., a patient).

In FIG. 9, a caregiver is considered to be interacting with an asset when the proximity area (e.g., proximity area 906a) generated by their beacon badge 906 overlaps with the proximity area 904a generated by the source beacon tag 904 placed on the asset. For example, the proximity area 906a (e.g., corresponding to the caregiver) is overlapping with the proximity area 904a (e.g., corresponding to the patient), and, thus, the caregiver is determined to be proximate to the patient and interacting with the patient. In this example, because the proximity area 906a (e.g., corresponding to the caregiver) does not overlap with example proximity area 902 (e.g., generated by the beacon tag 902), the caregiver is considered to not be interacting with the equipment on which the beacon tag 902 is placed. Furthermore, because of the interactions information, it can also be determined where the caregiver was positioned while interacting with the patient.

Figure 10:
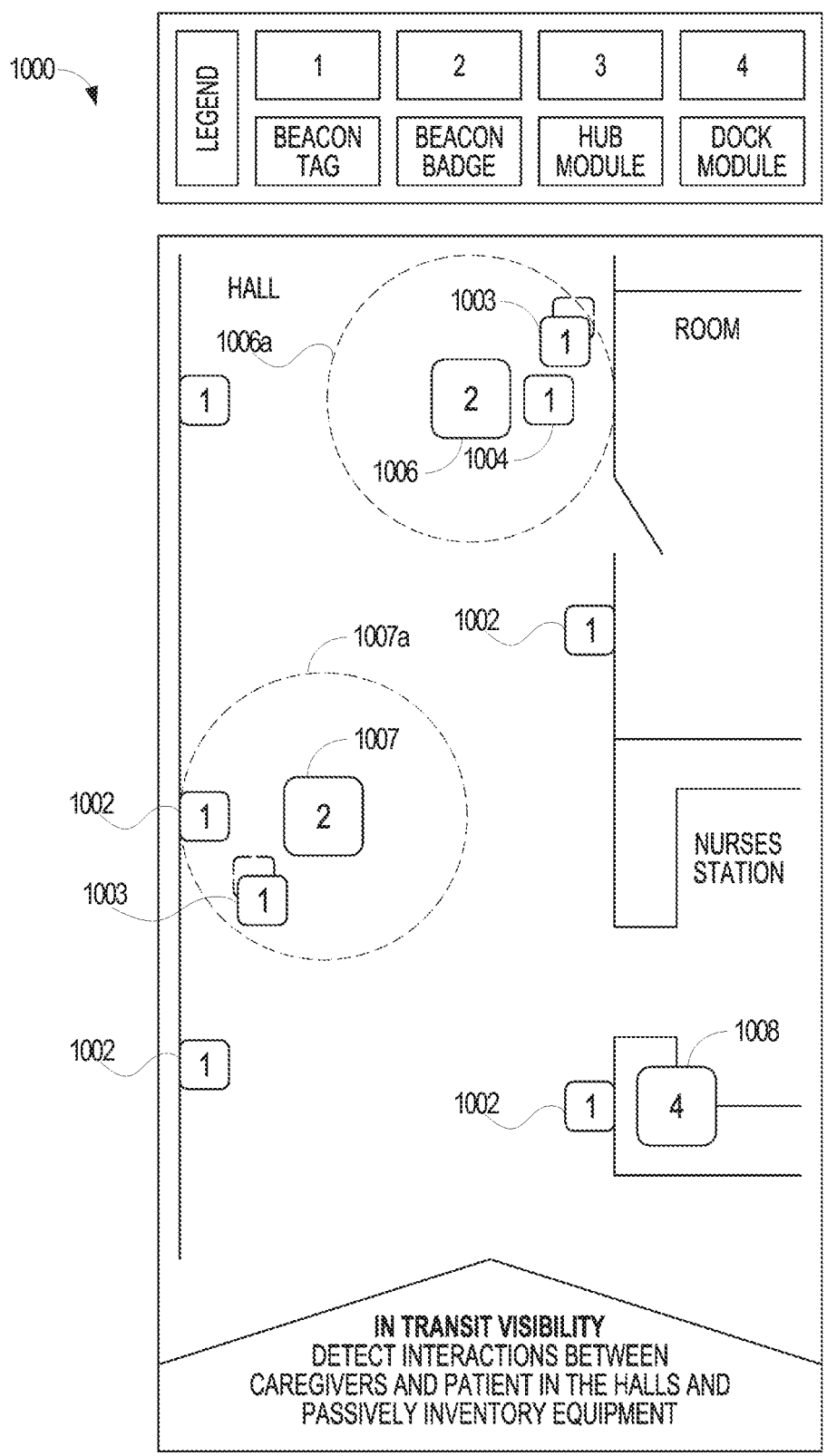
FIG. 10 illustrates another example environment to facilitate proximity detection and location tracking using a mobile wireless bridge, according to another example embodiment.

FIG. 10 illustrates another example environment 1000 to facilitate proximity detection and location tracking using a mobile wireless bridge 402, according to another example embodiment. In particular, and in the context of providing healthcare, FIG. 10 illustrates an example transit environment 1000 (e.g., a hallway) in which one or more caregivers may be interacting with assets. The transit environment 1000 includes beacon tags 1002 positioned at different locations in the transit environment 1000, a beacon tag 1003 positioned on equipment, and a beacon tag 1004 positioned on a patient.

Various beacon badges 1006, 1007 are provided to caregivers to wear throughout their normal workflow. The transit environment 1000 also includes a dock module 1008 to which one or more of the beacon badges 1006, 1007 are coupled (e.g., for charging).

As a caregiver walks through the transit environment 1000, the interactions between the beacon tags 1002-1003 and beacon badges 1006,1007 are used to determine that the caregiver is proximate to and interacting with different assets based on, for example, overlapping proximity areas. For example, overlap between the proximity area 1006a and the proximity area generated by the beacon tag 1003 can be used to determine when the caregiver is proximate to equipment on which the beacon tag 1003 resides (e.g., a telemetry unit, a wheelchair, etc.). As another example, overlap between the proximity area 1006a and the proximity area generated by the beacon tag 1004 can be used to determine when the caregiver is proximate to and/or interacting with a patient. As a further example, overlap between example proximity area 1007a (e.g., generated by the beacon badge 1007) and the proximity area generated by the beacon tag 1002 can be used to determine when the caregiver is proximate to a location (e.g., a wall, a doorway, etc.), etc. In this manner, the interactions between the beacon badges 1006, 1007 and the beacon tags 1002-1004 indicate where a given caregiver is relative to other items in the environment 1000.

Figure 11:
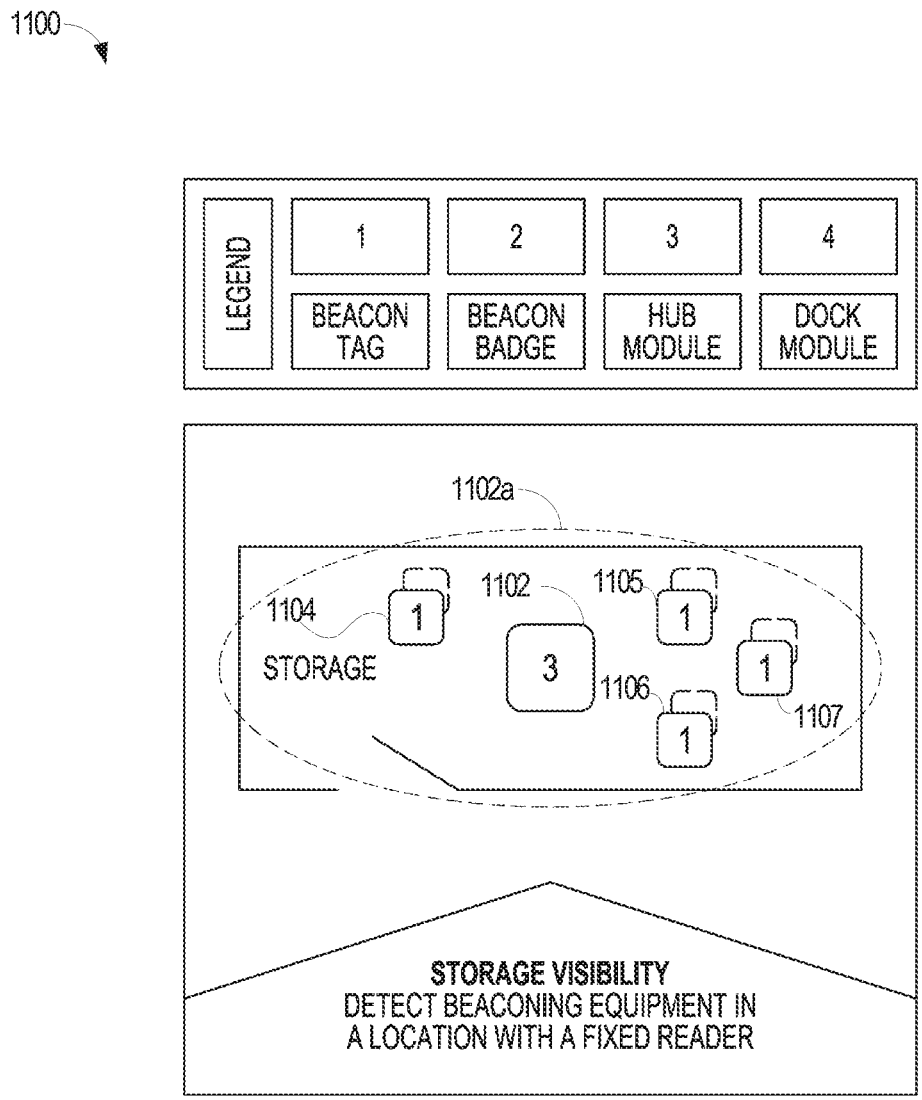
FIG. 11 illustrates yet a further environment to facilitate proximity detection and location tracking using a mobile wireless bridge, according to a further embodiment.

FIG. 11 illustrates yet a further environment 1100 to facilitate proximity detection and location tracking using a mobile wireless bridge 402, according to a further embodiment. In particular, FIG. 11 illustrates a storage environment 1100 that includes a hub module 1102, having a proximity area 1102*a*, and beacon tags 1104-1107 placed on different equipment. In the context of healthcare, such equipment might include IV pumps, wheelchairs, telemetry units, etc. In the context of other environments, such as retail, such equipment might include cash registers, office supplies, chairs, tables, signage, and other such equipment.

In FIG. 11, a beacon badge (not shown) may be coupled to the hub module 1102, thereby causing the hub module 1102 to detect proximate assets (e.g., the respective equipment on which the beacon tags 1104-1107 are placed). Using the coupling of the beacon badge to the hub module 1102, the interactions between the hub module 1102 and the beacon tags 1104-1107 can be used to determine when equipment is removed from the storage environment 1100 (e.g., the proximity area of the beacon tag 1104-1107 affixed to the equipment does not overlap with the proximity area 1102*a* of the hub module 1102). Through these interactions, it can also be determined when an asset is moved into the storage environment 1100 (e.g., the proximity area of the beacon tag 1104-1107 affixed to the equipment being placed into storage overlaps with the proximity area 1102*a*).

Figure 12:
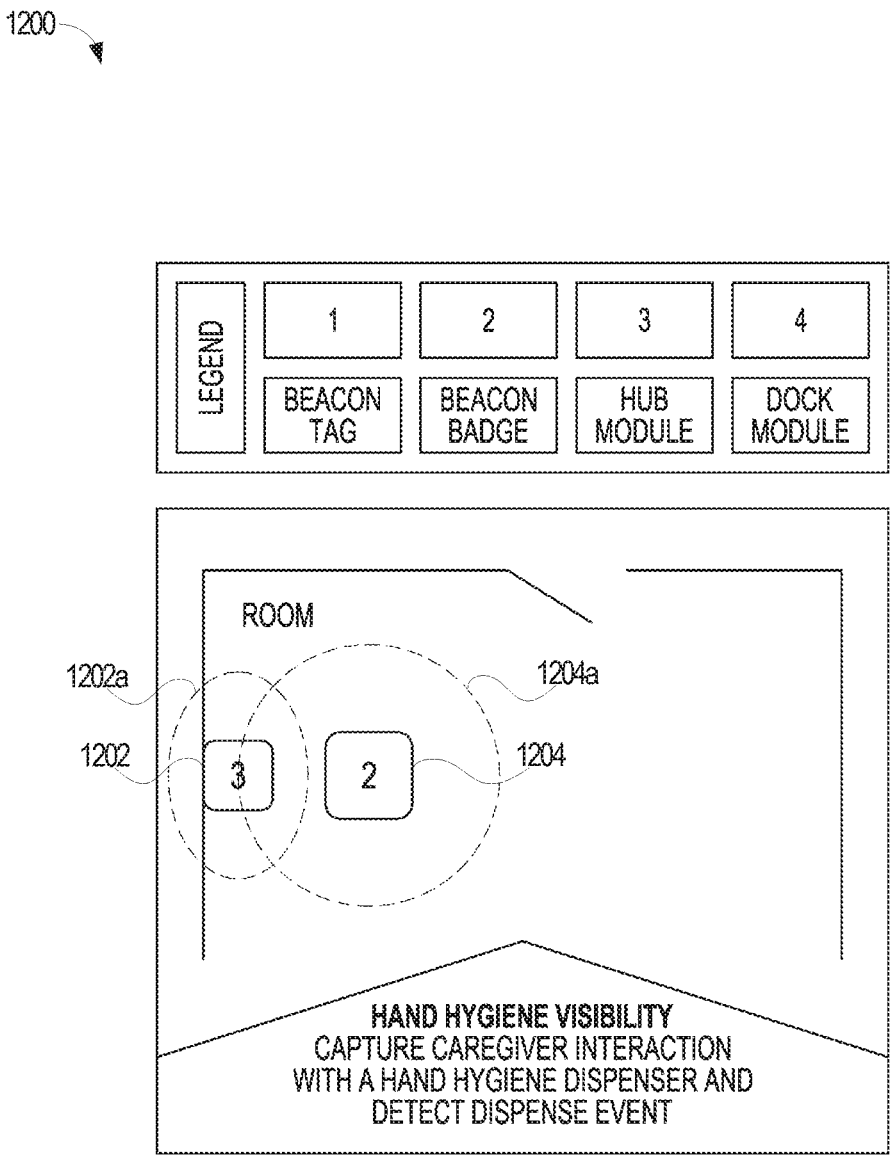
FIG. 12 illustrates another environment to facilitate proximity detection and location tracking using a mobile wireless bridge, according to another embodiment.

FIG. 12 illustrates another environment 1200 to facilitate proximity detection and location tracking using a mobile wireless bridge 402, according to another embodiment. In particular, and in the context of healthcare, FIG. 12 illustrates a hand hygiene dispensing environment 1200. In the environment 1200, a hub module 1202 is positioned on (or near) a hand hygiene dispenser (e.g., a soap dispenser) and generates a proximity area 1202*a*. The environment 1200 also includes a caregiver wearing a beacon badge 1204, which generates a proximity area 1204*a*. In FIG. 12, when the proximity area 1202*a* and the proximity area 1204*a* overlap, an interaction is detected. For example, the beacon badge 1204 receives a beacon message 406*a*-409*a* from the beacon tag 1104-1107 coupled to the hub module 1202, and determines an RSSI value corresponding to the received beacon message 406*a*-409*a*. The reception of the beacon message 406*a*-409*a* may be considered an interaction with the beacon tag 1104-1107 coupled to the hub module 1202. In addition, a dispense event may also be detected based on, for example, additional sensors included in the hub module 1202 and/or based on a predetermined time threshold in which the beacon badge 1204 is in proximity to the hub module 1202.

Figure 13:
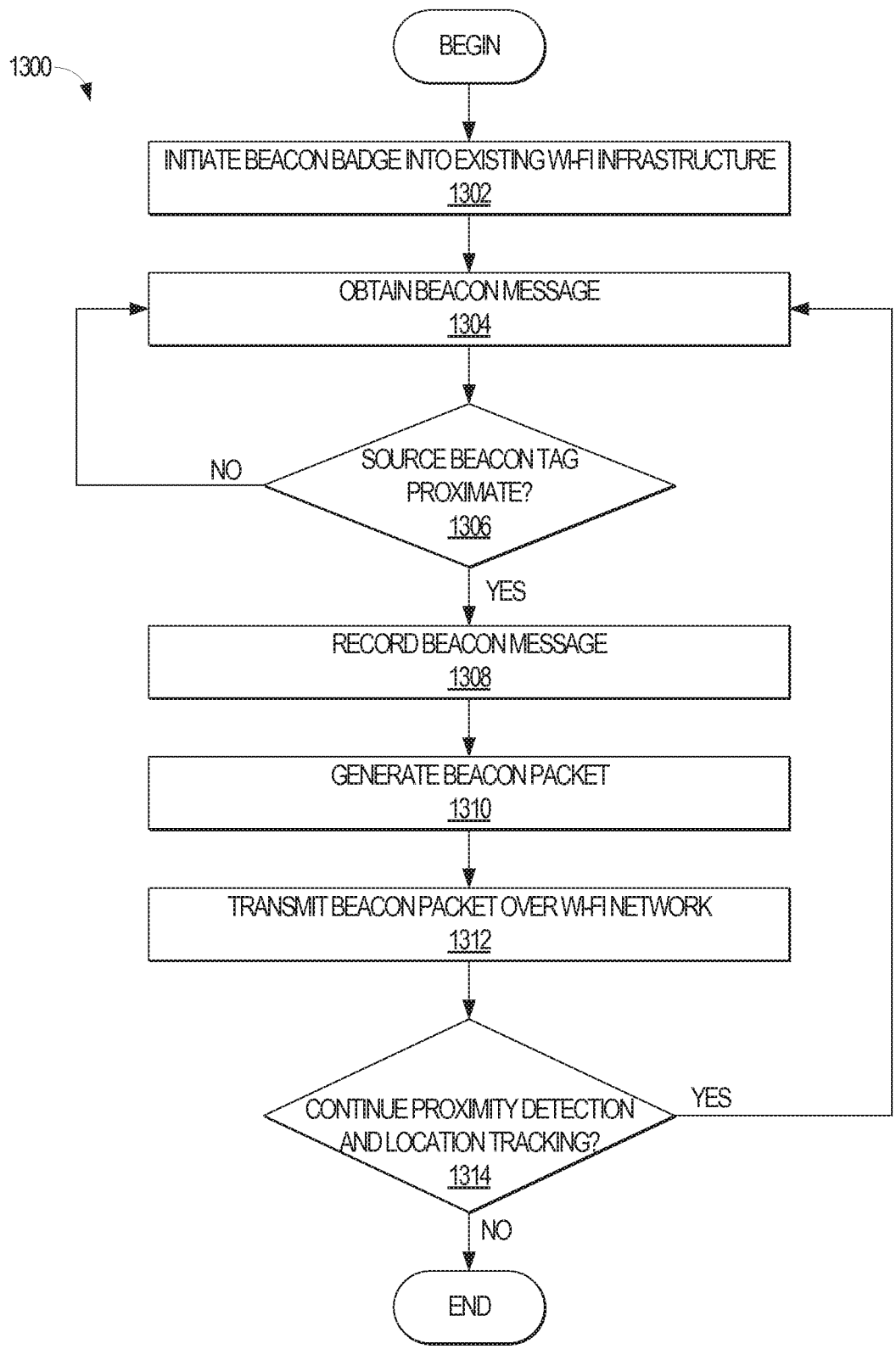
FIG. 13 illustrates a method for operating the disclosed wireless bridge, according to an example embodiment.

FIG. 13 illustrates a method 1300 for operating the disclosed wireless bridge 402 according to an example embodiment. The method 1300 is implemented by one or more of a beacon tag 502, a beacon module, a hub module 506, and/or a dock module 508, and is discussed by way of reference thereto. Method 1300 begins at block 1302 when the beacon badge 402 (FIG. 4) is initiated. For example, the beacon badge 402 may be configured to communicate with the example RTLS server 404 (FIG. 4) via the network 410 (FIG. 4). At block 1304, the beacon badge 402 obtains a beacon message (e.g., the example beacon messages 406*a*-409*a* (FIG. 4)). For example, the beacon badge 402 may include an IR sensor 606 and/or a BLE chip 608 to receive beacon messages 406*a*-409*a* broadcast using BLE technology. At block 1306, the beacon badge 402 determines whether the source beacon tag 502 corresponding to the obtained beacon message 406*a*-409*a* is proximate. For example, the beacon badge 402 may include the proximity engine 624 (FIG. 6), and determine an RSSI value for the received beacon message 406*a*-409*a*. If, at block 1306, the proximity engine 624 determines the source beacon tag 502 is not proximate to the beacon badge 504 (e.g., the RSSI value did not satisfy a proximity threshold), then, the beacon message 406*a*-409*a* is discarded and control returns to block 1304 to wait to obtain another beacon message 406*a*-409*a*.

If, at block 1306, the proximity engine 624 determines that the source beacon tag 502 is proximate to the beacon badge 504 (e.g., the RSSI value satisfied the proximity threshold), then, at block 1308, the proximity engine 624 records the beacon message 406*a*-409*a*. For example, the proximity engine 624 may log the unique identifier and location information included in the obtained beacon message 406*a*-409*a*. The example proximity engine 624 may also append a timestamp and an RSSI value to the record. At block 1310, the proximity engine 624 generates the example beacon packet 412 (FIG. 4). For example, the proximity engine 624 aggregates the records for beacon messages 406*a*-409*a* obtained over a period. In some examples, the proximity engine 624 generates the beacon packet 412 in response to receiving the beacon message 406*a*-409*a*. At block 1312, the proximity engine 624 transmits the beacon packet 412 to the RTLS server 404 (FIG. 4) over the Wi-Fi network 410. At block 1314, the proximity engine 624 determines whether to continue proximity detection and location tracking in the environment. For example, the motion sensor 616 and/or IMU chip 618 may determine that the beacon badge 402 is at rest for a threshold period. If, at block 1314, the proximity engine 624 determined to continue proximity detection and location tracking, then control returns to block 1304 to wait to obtain another beacon message 406*a*-409*a*. If, at block 1314, the proximity engine 624 determined to stop proximity detection and location tracking, then the method 1300 ends.

Figure 14:
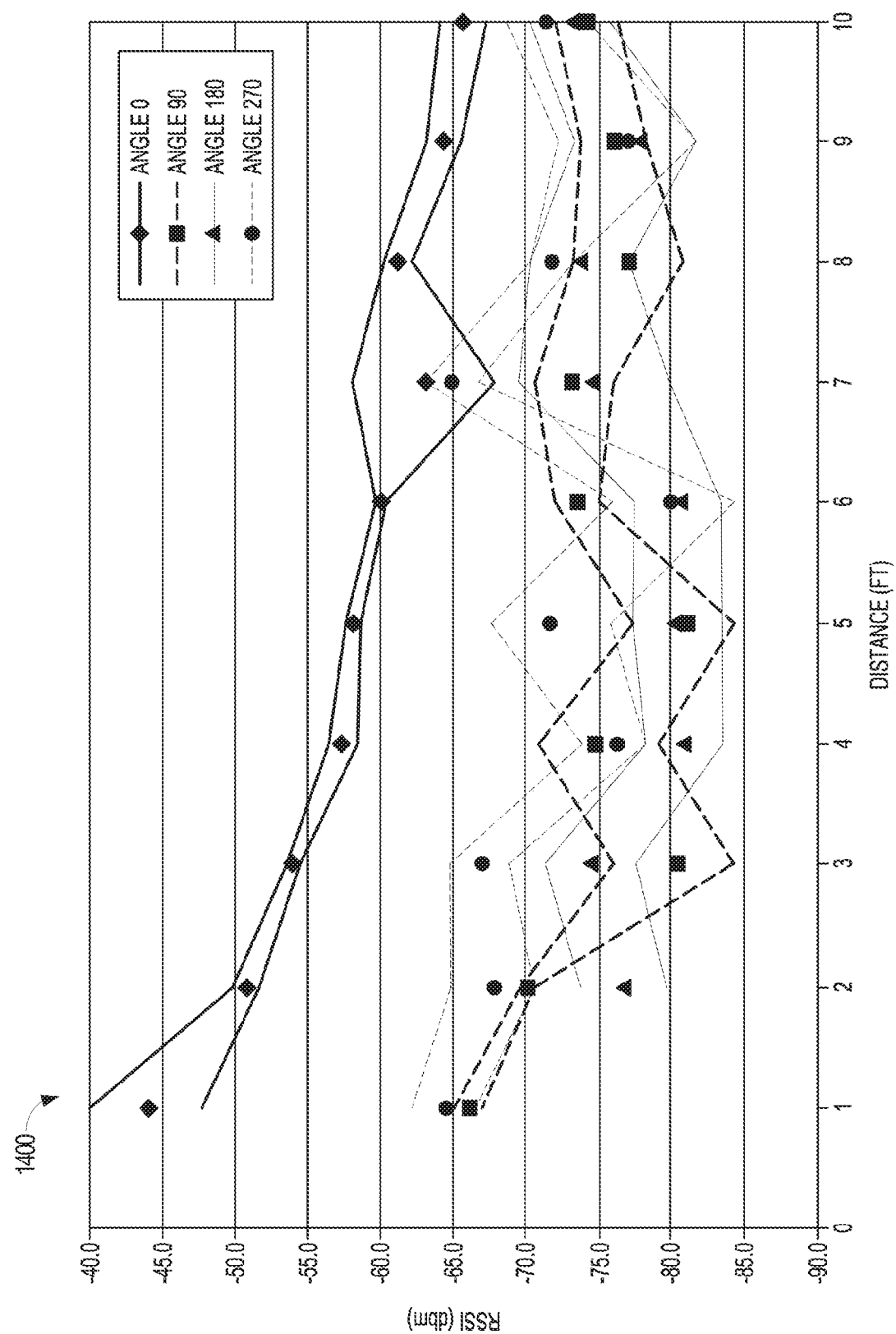
FIG. 14 is a graph correlating average RSSI values with distance based on the angle that a beacon badge receives a signal from a beacon tag.

FIG. 14 is graph 1400 correlating average RSSI values with distance based on the angle at a beacon badge 402 receives a signal from a beacon tag 502. In FIG. 14, the graph 1400 also displays the 95% upper and lower bounds of the RSSI values measured at different distances.

In operation, a real-time location service (RTLS) system can be used for proximity detection and location tracking in various types of environments, such as retail stores, factory floors, hospitals, industrial centers, and other such environments. The RTLS system disclosed herein may be used to track the location of assets (e.g., equipment, tools, merchandise, inventory, supplies, personnel, patients, employees, etc.) within the environment. To track the location of the assets, the RTLS system includes beacon tags 502 placed (e.g., positioned on, affixed to, coupled with, etc.) on the respective assets. The beacon tags 502 periodically broadcast a beacon message 406*a*-409*a* including identification information for the corresponding source beacon tag 502. For example, a beacon message 406*a*-409*a* may include a unique identifier and location information for the beacon tag 502 that broadcast the beacon message 406*a*-409*a*.

The disclosed RTLS system also includes one or more beacon badges 402, which may be worn by personnel moving through or working in the environment. The beacon badges 402 include an IR sensor 606 and/or a BLE chip 608 to receive the broadcast beacon messages 406*a*-409*a*. As the personnel move about the environment, their respective beacon badges 402 obtain beacon messages 406*a*-409*a*. In certain embodiments, the beacon badge 402 includes a proximity engine 624 to manage the obtained beacon messages 406a-409a. For example, the proximity engine 624 may determine an RSSI value for an obtained message and compare the RSSI value to a proximity threshold. If the RSSI value does not satisfy the proximity threshold, the beacon message 406a-409a may be discarded by the proximity engine 624. In other examples, if the RSSI value does satisfy the proximity threshold, the proximity engine 624 records information included in the beacon message 406a-409a such as the unique identifier and the location information. In certain embodiments, the proximity engine 624 may also log a timestamp indicative of when the beacon message 406a-409a was received and the RSSI value for the beacon message 406a-409a. Periodically and/or aperiodically, the proximity engine 624 generates a beacon packet 412 from the recorded beacon messages 406a-409a.

In certain embodiments, the proximity engine 624 transmits the beacon packets 412 over a wireless network 410 to an RTLS server 404. Using the environment's wireless network 410 to transmit the beacon packets 412 helps manage costs for the RTLS system, as a new network infrastructure does not need to be built or implemented. The RTLS server 404 aggregates the beacon packets 412 received from one or more beacon badges 402 in the environment and generates reports based on the received beacon packets 412. For example, an asset (e.g., a wheelchair, a jackhammer, an article of clothing, etc.) may be "tagged" with a beacon tag 502 having a unique identifier. When the location of the asset needs to be determined, the RTLS server 404 can generate a report identifying the beacon messages 406a-409a with the matching unique identifier and identify the location of the asset. For example, the RTLS server 404 can determine whether the asset is being moved, the last time a given personnel was near the asset, or where the asset is likely to be located.

In some examples, the RTLS systems may detect proximity and interaction with assets in the environment. In one embodiment, hub modules 506 enable coupling a beacon badge 402 to an extension having an external power source. For example, a hub module 506 may be positioned on a doorway, a shelf, a ledge, in a room, or elsewhere within the environment. The hub module 506 also includes an AC/DC connection to draw power. By coupling the beacon badge 402 to the hub module 506, the battery life of the beacon badge 402 can be extended. In certain embodiments, the beacon badge 402 is coupled to the hub module 506 so that the hub module 506 receives beacon messages 406a-409a as assets move near the hub. For example, an employee may be provided with an identification tag that includes a beacon tag 502. When the employee moves near a doorway or other asset, the hub module 506 receives beacon messages 406a-409a broadcast by the beacon tag 502. Using the received beacon messages 406a-409a, it can be determined where the employee is going.

In certain embodiments, the proximity engine 624 included in the beacon badge 402 may determine whether a source beacon tag 502 is proximate to the beacon badge 402. For example, when the proximity area of the beacon tag 502 overlaps with the proximity area of the beacon badge 402, a determination can be made that an employee wearing the beacon badge 402 is proximate and/or interacting with the asset on which the beacon tag 502 is placed.

Although examples disclosed herein include the proximity engine 624 in the beacon badge 402, the proximity engine 624 may additionally or alternatively be included with the RTLS server 404. For example, if the beacon badge 402 does not include a proximity engine 624, the beacon badge 402 can transmit beacon packets 412 as a beacon message 406a-409a is received. In some such examples, the RTLS server 404 may process the beacon packets 412 and determine whether to discard the corresponding beacon message 406a-409a information and/or detect proximity of beacon tags 502 with beacon badges 402. In some examples, the beacon badge 402 may include proximity engine 624 to filter out beacon messages 406a-409a received with weak RSSI values, and the RTLS server 404 may include a proximity engine 624 to determine when a beacon badge 402 and a beacon tag 502 are proximate.

Modules, Components, and Logic

Certain embodiments are described herein as including logic or a number of components, modules, or mechanisms. Modules may constitute either software modules (e.g., code embodied on a machine-readable medium) or hardware modules. A "hardware module" is a tangible unit capable of performing certain operations and may be configured or arranged in a certain physical manner. In various example embodiments, one or more computer systems (e.g., a stand-alone computer system, a client computer system, or a server computer system) or one or more hardware modules of a computer system (e.g., a processor 130 or a group of processors 130) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an application specific integrated circuit (ASIC). A hardware module may also include programmable logic or circuitry that is temporarily configured by software to perform certain operations. For example, a hardware module may include software executed by a general-purpose processor 130 or other programmable processor 130. Once configured by such software, hardware modules become specific machines (or specific components of a machine) uniquely tailored to perform the configured functions and are no longer general-purpose processors 130. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor 130 configured by software to become a special-purpose processor, the general-purpose processor 130 may be configured as respectively different special-purpose processors (e.g., comprising different hardware modules) at different times. Software accordingly configures a particular processor or processors 130, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors 130 that are temporarily configured (e.g., by software) or permanently configured to perform the relevant operations. Whether temporarily or permanently configured, such processors 130 may constitute processor-implemented modules that operate to perform one or more operations or functions described herein. As used herein, "processor-implemented module" refers to a hardware module implemented using one or more processors 130.

Similarly, the methods described herein may be at least partially processor-implemented, with a particular processor or processors 130 being an example of hardware. For example, at least some of the operations of a method may be performed by one or more processors 130 or processor-implemented modules. Moreover, the one or more processors 130 may also operate to support performance of the relevant operations in a "cloud computing" environment or as a "software as a service" (SaaS). For example, at least some of the operations may be performed by a group of computers (as examples of machines including processors 130), with these operations being accessible via a network 410 (e.g., the Internet) and via one or more appropriate interfaces (e.g., an application program interface (API)).

The performance of certain of the operations may be distributed among the processors 130, not only residing within a single machine, but deployed across a number of machines. In some example embodiments, the processors 130 or processor-implemented modules may be located in a single geographic location (e.g., within a home environment, an office environment, or a server farm). In other example embodiments, the processors 130 or processor-implemented modules may be distributed across a number of geographic locations.

Machine and Software Architecture

The modules, methods, applications and so forth described in conjunction with FIGS. 1-15 are implemented in some embodiments in the context of a machine and an associated software architecture. The sections below describe representative software architecture(s) and machine (e.g., hardware) architecture(s) that are suitable for use with the disclosed embodiments.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture may yield a smart device for use in the "interne of things." While yet another combination produces a server computer for use within a cloud computing architecture. Not all combinations of such software and hardware architectures are presented here as those of skill in the art can readily understand how to implement the invention in different contexts from the disclosure contained herein.

Example Machine Architecture and
Machine-Readable Medium

Figure 15:
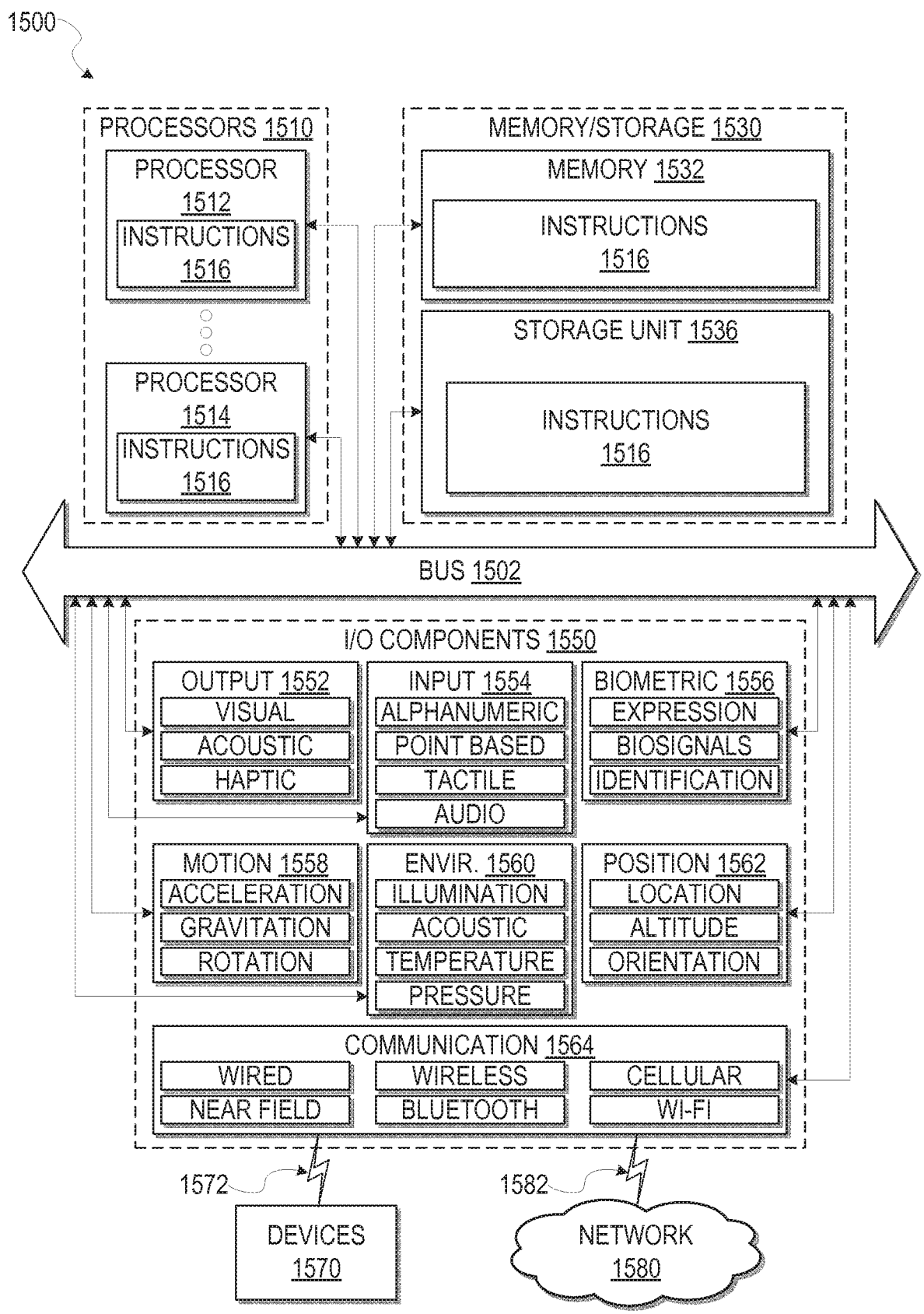
FIG. 15 illustrates a diagrammatic representation of a machine in the form of a computer system within which a set of instructions may be executed for causing the machine to perform any one or more of the methodologies discussed herein, according to an example embodiment.

FIG. 15 is a block diagram illustrating components of a machine 1500, according to some example embodiments, able to read instructions from a machine-readable medium (e.g., a machine-readable storage medium) and perform any one or more of the methodologies discussed herein. Specifically, FIG. 15 shows a diagrammatic representation of the machine 1500 in the example form of a computer system, within which instructions 1516 (e.g., software, a program, an application, an applet, an app, or other executable code) for causing the machine 1500 to perform any one or more of the methodologies discussed herein may be executed. For example, the instructions 1516 may cause the machine 1500 to execute the flow diagrams of FIG. 13. Additionally, or alternatively, the instructions 1516 may implement one or more of the components shown in FIGS. 5-6, and so forth. The instructions 1516 transform the general, non-programmed machine 1500 into a particular machine programmed to carry out the described and illustrated functions in the manner described. In alternative embodiments, the machine 1500 operates as a standalone device or may be coupled (e.g., networked) to other machines. In a networked deployment, the machine 1500 may operate in the capacity of a server machine or a client machine in a server-client network environment, or as a peer machine in a peer-to-peer (or distributed) network environment. The machine 1500 may comprise, but not be limited to, a server computer, a client computer, a personal computer (PC), a tablet computer, a laptop computer, a personal digital assistant (PDA), a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1516, sequentially or otherwise, that specify actions to be taken by machine 1500. Further, while only a single machine 1500 is illustrated, the term "machine" shall also be taken to include a collection of machines 1500 that individually or jointly execute the instructions 1516 to perform any one or more of the methodologies discussed herein.

The machine 1500 may include processors 1510, memory 1530, and I/O components 1550, which may be configured to communicate with each other such as via a bus 1502. In an example embodiment, the processors 1510 (e.g., a central processing unit (CPU), a reduced instruction set computing (RISC) processor, a complex instruction set computing (CISC) processor, a graphics processing unit (GPU), a digital signal processor (DSP), an application specific integrated circuit (ASIC), a radio-frequency integrated circuit (RFIC), another processor, or any suitable combination thereof) may include, for example, processor 1512 and processor 1514 that may execute instructions 1516. The term "processor" is intended to include multi-core processors 1510 that may comprise two or more independent processors 1512, 1514 (sometimes referred to as "cores") that may execute instructions 1516 contemporaneously. Although FIG. 15 shows multiple processors 1512, 1514, the machine 1500 may include a single processor 1512 with a single core, a single processor 1512 with multiple cores (e.g., a multi-core processor), multiple processors 1512, 1514 with a single core, multiple processors 1512, 1514 with multiples cores, or any combination thereof.

The memory/storage 1530 may include a memory 1532, such as a main memory, or other memory storage, and a storage unit 1536, both accessible to the processors 1510 such as via the bus 1502. The storage unit 1536 and memory 1532 store the instructions 1516 embodying any one or more of the methodologies or functions described herein. The instructions 1516 may also reside, completely or partially, within the memory 1532, within the storage unit 1536, within at least one of the processors 1510 (e.g., within the processor's cache memory), or any suitable combination thereof, during execution thereof by the machine 1500. Accordingly, the memory 1532, the storage unit 1536, and the memory of processors 1510 are examples of machine-readable media.

As used herein, "machine-readable medium" means a device able to store instructions 1516 and data temporarily or permanently and may include, but is not be limited to, random-access memory (RAM), read-only memory (ROM), buffer memory, flash memory, optical media, magnetic media, cache memory, other types of storage (e.g., erasable programmable read-only memory (EEPROM)) and/or any suitable combination thereof. The term "machine-readable medium" should be taken to include a single medium or multiple media (e.g., a centralized or distributed database, or associated caches and servers) able to store instructions 1516. The term "machine-readable medium" shall also be taken to include any medium, or combination of multiple media, that is capable of storing instructions (e.g., instructions 1516) for execution by a machine (e.g., machine 1500), such that the instructions 1516, when executed by one or more processors o f the machine 1500 (e.g., processors 1510), cause the machine 1500 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1550 may include a wide variety of components to receive input, provide output, produce output, transmit information, exchange information, capture measurements, and so on. The specific I/O components 1550 that are included in a particular machine 1500 will depend on the type of machine. For example, portable machines such as mobile phones will likely include a touch input device or other such input mechanisms, while a headless server machine will likely not include such a touch input device. It will be appreciated that the I/O components 1550 may include many other components that are not shown in FIG. 15. The I/O components 1550 are grouped according to functionality merely for simplifying the following discussion and the grouping is in no way limiting. In various example embodiments, the I/O components 1550 may include output components 1552 and input components 1554. The output components 1552 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1554 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor 616, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1550 may include biometric components 1556, motion components 1558, environmental components 1560, or position components 1562 among a wide array of other components. For example, the biometric components 1556 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1558 may include acceleration sensor components (e.g., accelerometer), gravitation sensor components, rotation sensor components (e.g., gyroscope), and so forth. The environmental components 1560 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1562 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1550 may include communication components 1564 operable to couple the machine 1500 to a network 1580 or devices 1570 via coupling 1582 and coupling 1572 respectively. For example, the communication components 1564 may include a network interface component or other suitable device to interface with the network 1580. In further examples, communication components 1564 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 1570 may be another machine or any of a wide variety of peripheral devices (e.g., a peripheral device coupled via a Universal Serial Bus (USB)).

Moreover, the communication components 1564 may detect identifiers or include components operable to detect identifiers. For example, the communication components 1564 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1564, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 1580 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the public switched telephone network (PSTN), a plain old telephone service (POTS) network, a cellular telephone network, a wireless network, a Wi-Fi® network, another type of network, or a combination of two or more such networks. For example, the network 1580 or a portion of the network 1580 may include a wireless or cellular network and the coupling 1582 may be a Code Division Multiple Access (CDMA) connection, a Global System for Mobile communications (GSM) connection, or other type of cellular or wireless coupling. In this example, the coupling 1582 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile-Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1516 may be transmitted or received over the network 1580 using a transmission medium via a network interface device (e.g., a network interface component included in the communication components 1564) and utilizing any one of a number of well-known transfer protocols (e.g., hypertext transfer protocol (HTTP)). Similarly, the instructions 1516 may be transmitted or received using a transmission medium via the coupling 1572 (e.g., a peer-to-peer coupling) to devices 1570. The term "transmission medium" shall be taken to include any intangible medium that is capable of storing, encoding, or carrying instructions 1516 for execution by the machine 1500, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

We claim:

1. A location hub apparatus arranged at a first location, the apparatus comprising:
   memory including instructions to be executed;
   a communication interface to receive and transmit via at least a first communication technology and a second communication technology;
   at least one processor to execute the instructions to at least:
   receive, via a first communication technology, a message from a beacon at a second location within a proximity area of the apparatus, the message indicative of the second location and identifying the beacon; and
   relay, via a second communication technology, the message to a location server to determine asset location, wherein the second communication technology is different from the first communication technology; and a power source drawing external power for the memory, the communication interface, and the at least one processor.

2. The apparatus of claim 1, wherein the at least one processor is to receive a plurality of messages and batch the plurality of messages according to at least one of a) a number of messages or b) a time period before sending the batch of received messages to the location server.

3. The apparatus of claim 1, wherein the message includes a timestamp and a received signal strength indication.

4. The apparatus of claim 3, wherein the at least one processor is to determine a proximity of the beacon to the apparatus by comparing the received signal strength indication to a threshold associated with the proximity area and is to discard the message when the received signal strength indication is less than the threshold.

5. The apparatus of claim 1, wherein the communication interface is to receive and transmit using wireless communication.

6. The apparatus of claim 5, wherein the wireless communication includes at least one of Bluetooth™ and Wi-Fi communication.

7. The apparatus of claim 1, wherein the second location is identified in the message using at least one of spatial coordinates or a location identifier.

8. The apparatus of claim 1, wherein the message enables tracking of asset interaction with fixed locations.

9. The apparatus of claim 8, wherein the fixed locations include at least one of soap dispensers, beds, walls, or equipment.

10. The apparatus of claim 1, wherein the apparatus is at least one of incorporated into or affixed to an asset.

11. The apparatus of claim 1, wherein the memory is to store an identifier for the apparatus, the identifier to be relayed to the location server with the message.

12. The apparatus of claim 1, wherein the memory, the communication interface, and the at least one processor are incorporated in a system on a chip.

13. The apparatus of claim 1, further including a sensor to detect an event.

14. The apparatus of claim 13, wherein the event includes at least one of patient movement, asset movement, or hand hygiene dispensing.

15. The apparatus of claim 13, wherein the at least one processor is to infer an event based on movement of the beacon in the proximity area.

16. The apparatus of claim 13, wherein the sensor includes a motion sensor.

17. The apparatus of claim 1, further including an internal management unit to manage power utilization of the apparatus.

18. A system comprising:
a hub module communicatively coupled to a wireless receiver, a wireless transmitter, and an external power source; and a beacon tag including a wireless transmitter, the wireless transmitter configured to broadcast at least one wireless message, the at least one wireless message being broadcast using a first wireless protocol, wherein the hub module is configured to receive the at least one wireless message through the wireless receiver, determine a proximity of a beacon tag to the hub module by comparing a received signal strength indication to a threshold associated with a proximity area, and discard the at least one wireless message when the received signal strength indication is less than the threshold.

19. The system of claim 18, wherein the wireless transmitter of the hub module is configured to use a second wireless protocol to send a second wireless message, and wherein the first wireless protocol and the second wireless protocol are different wireless protocols.

20. The system of claim 19, further including a real-time location services (RTLS) server in communication with the hub module, the RTLS server being configured to determine a location of the beacon tab in relation to the hub module.

21. The system of claim 18, wherein the hub module is affixed to a stationary or near stationary surface.

22. A location hub apparatus arranged at a first location, the location hub apparatus comprising:

memory including instructions to be executed;

a communication interface to receive and transmit data via at least a first communication technology and a second communication technology;

at least one processor to execute the instructions to at least:

receive, via the first communication technology, a message from a beacon at a second location within a proximity area of the location hub apparatus, the message indicative of the second location and identifying the beacon;

determine a proximity of the beacon to the location hub apparatus by comparing a received signal strength indication to a threshold associated with the proximity area, and discard the message when the received signal strength indication is less than the threshold; and relay, via a second communication technology, the message to a location server to determine asset location when the received signal strength indication is equal to or greater than the threshold.

* * * * *